(12) United States Patent
Jerse et al.

(10) Patent No.: US 10,414,805 B2
(45) Date of Patent: Sep. 17, 2019

(54) GONORRHEAL MTRE PEPTIDES AND VACCINES

(71) Applicant: The Henry M. Jackson Foundation for the Advancement of Military Medicine, Inc., Bethesda, MD (US)

(72) Inventors: Ann Jerse, Rockville, MD (US); Amanda DeRocco, Garrett Park, MD (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 0 days.

(21) Appl. No.: 15/905,479

(22) Filed: Feb. 26, 2018

(65) Prior Publication Data
US 2019/0077837 A1 Mar. 14, 2019

Related U.S. Application Data

(63) Continuation of application No. 14/442,832, filed as application No. PCT/US2013/070310 on Nov. 15, 2013, now Pat. No. 9,902,756.

(60) Provisional application No. 61/727,451, filed on Nov. 16, 2012.

(51) Int. Cl.
| C07K 14/22 | (2006.01) |
| A61K 39/095 | (2006.01) |
| C07K 16/12 | (2006.01) |
| A61K 38/00 | (2006.01) |
| A61K 39/00 | (2006.01) |

(52) U.S. Cl.
CPC ............ *C07K 14/22* (2013.01); *A61K 39/095* (2013.01); *C07K 16/1214* (2013.01); *C07K 16/1217* (2013.01); *A61K 38/00* (2013.01); *A61K 2039/543* (2013.01); *A61K 2039/55505* (2013.01); *C07K 2317/34* (2013.01)

(58) Field of Classification Search
None
See application file for complete search history.

(56) References Cited

FOREIGN PATENT DOCUMENTS

WO WO-02079243 A2 * 10/2002 ............ C07K 14/22

* cited by examiner

*Primary Examiner* — Brian Gangle
(74) *Attorney, Agent, or Firm* — Morgan, Lewis & Bockius LLP

(57) ABSTRACT

The invention is directed to MtrE peptides and their use in gonorrhea vaccines.

10 Claims, 6 Drawing Sheets

Specification includes a Sequence Listing.

GONORRHEAL MTRE PEPTIDES AND VACCINES

STATEMENT REGARDING FEDERALLY SPONSORED RESEARCH OR DEVELOPMENT

This invention was made with government support under A1031496 awarded by National Institutes of Health (NIH). The government has certain rights in the invention.

SEQUENCE LISTING SUBMISSION VIA EFS-WEB

A computer readable text file, entitled "SequenceListing.txt" created on or about Jun. 4, 2018 with a file size of about 16 kb contains the sequence listing for this application and is hereby incorporated by reference in its entirety.

BACKGROUND OF THE INVENTION

Field of the Invention

The invention is directed to MtrE peptides, including chimeric peptides comprising the MtrE peptides, and their use in gonorrhea vaccines.

Background of the Invention

Gonorrhea is the second most frequently reported infection to the Center for Disease Control (CDC) and, as such, accrues significant public health costs. Similarly, gonorrhea is the second most commonly reported infection in the U.S. military. Gonorrhea, like all sexually transmitted infections (STIs), disproportionately occurs in adolescents and young adults; therefore diagnosis and treatment of gonorrhea significantly taxes the public health care system. Serious morbidity arises, primarily in women, due to ascension of gonococcal infection to the endometrium and fallopian tubes, which leads to pelvic inflammatory disease (PID). PID and the post-infection complications, chronic pelvic pain, infertility and ectopic pregnancy, also occur at high incidence in the U.S. and worldwide. Ectopic pregnancy is a life-threatening condition and the fourth leading cause of maternal death in the U.S. Another cause for concern is the demonstration that gonococcal infection is associated with a risk for increased transmission of the human immunodeficiency virus (HIV).

Current prevention strategies for gonorrhea are limited to safe-sex counseling and the identification and treatment of infected individuals. Alarmingly, antibiotic resistance emerges rapidly in *Neisseria gonorrhoeae*, which threatens the current control measures. Only one class of antibiotics, the extended spectrum cephalosporins (ESCs), is left to treat gonococcal infections and therefore, this pathogen recently reached "super bug" status in 2007 (CDC, 2007). Since then, decreased susceptibility to ESCs has been reported, and in 2009 an ESC-resistant *N. gonorrhoeae* strain was isolated in Japan (CDC, 2011; Unemo, et al, 2010). The inability to treat gonorrhea may soon become a reality. Therefore, there is an urgent need for a gonorrhea vaccine.

The gonococcal MtrC-MtrD-MtrE (MtrCDE) active efflux pump is critical for experimental genital tract infection of female mice. Mutants in this pump are the most attenuated of all the mutants we have tested in this model. MtrC and MtrD are periplasmic and inner membrane proteins, respectively. The MtrE subunit, in contrast, is located in the bacterial outer membrane. Based on homology to other RND pumps and in silico analysis of the predicted secondary structure of the MtrE protein, it is likely that MtrE has two surface-exposed loops that could possibly be targeted for a vaccine.

SUMMARY OF THE INVENTION

The present application is directed to isolated MtrE peptides comprising an amino acid sequence that is at least 80% identical to residues 23-467 of SEQ ID NO:1, or an amino acid sequence that is at least 80% identical to residues 23-155 of SEQ ID NO:1 or an amino acid sequence that is at least 80% identical to residues 313-467 of SEQ ID NO:1.

The present invention is also directed to methods of producing isolated MtrE proteins, with the method comprising culturing a host cell harboring a vector coding for the MtrE protein in culture conditions in which expression of the MtrE protein from the vector occurs in the host, and purifying the MtrE protein from the cell culture.

The present invention also directed to pharmaceutical composition comprising the isolated MtrE proteins of the present invention and methods of immunizing a subject against *Neisseria gonorrhoeae* (*N. gonorrhoeae*) comprising administering the pharmaceutical compositions of the present invention in an immunogenically effective amount.

The present invention also relates to an antibody or antibody fragment that binds a MtrE protein in *Neisseria gonorrhoeae* (*N. gonorrhoeae*).

DETAILED DESCRIPTION OF THE INVENTION

Figure 1:
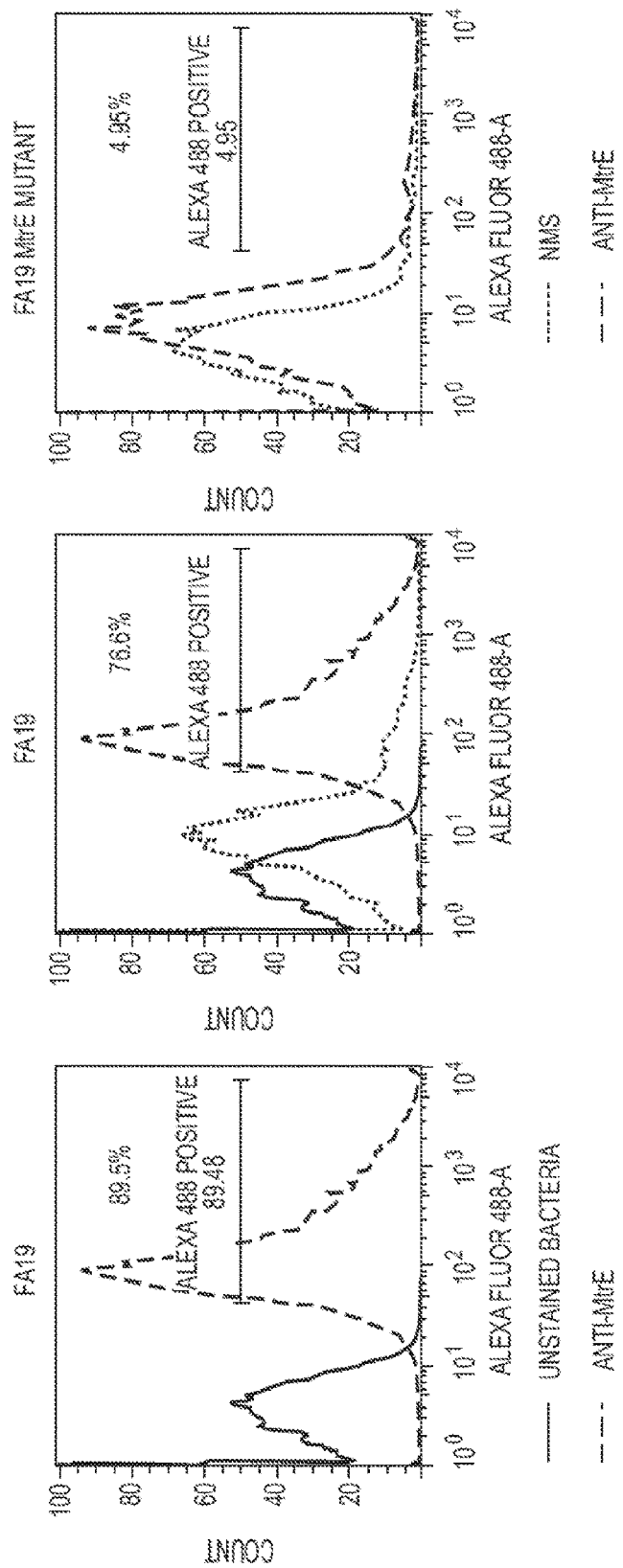
FIG. 1 depicts the binding of $MtrE_{21-467}$ specific antiserum to the surface of *N. gonorrhoeae*.
Figure 2:
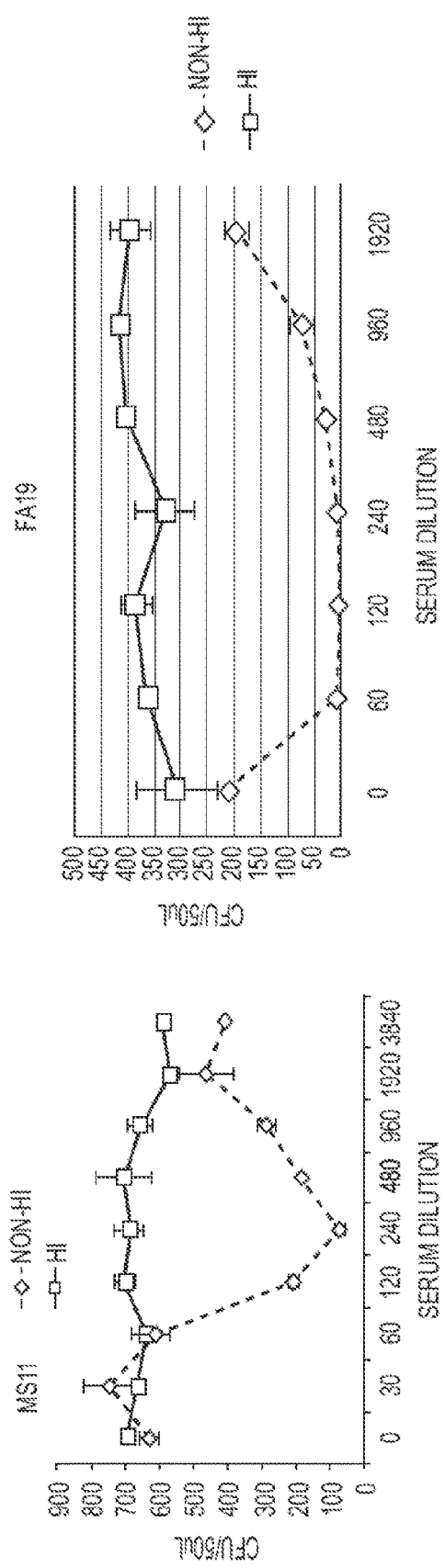
FIG. 2 depicts the bactericidal activity of $MtrE_{21-467}$ specific antiserum against three different gonococcal strains but not an MtrCDE-deficient mutant.
Figure 2:
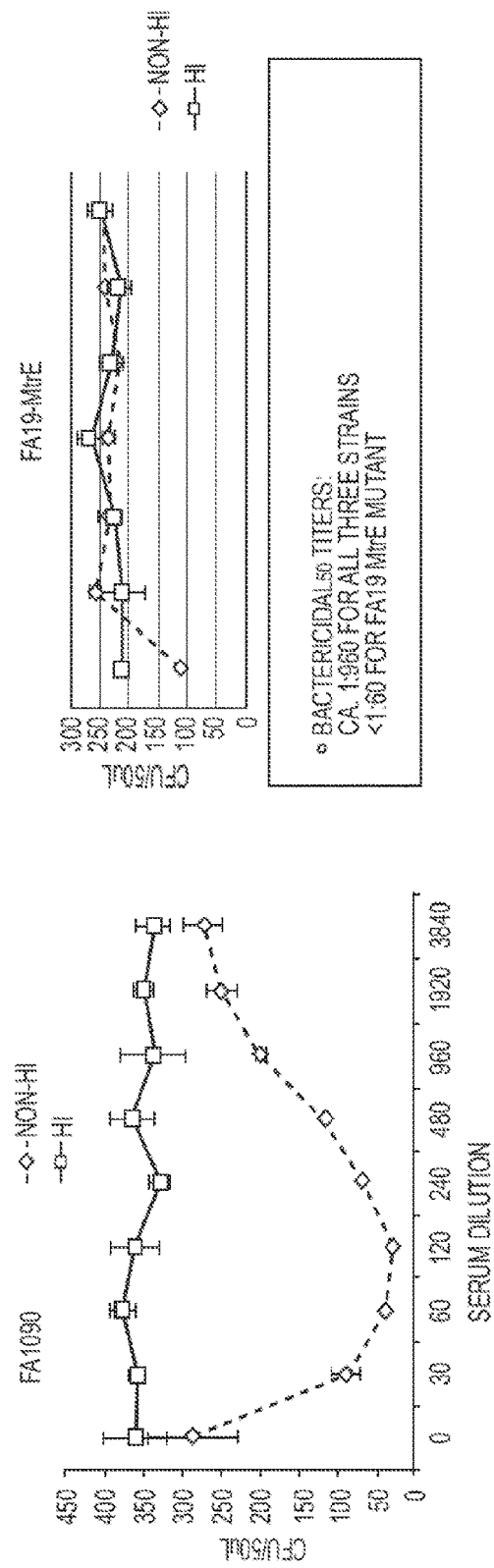
Figure 3:
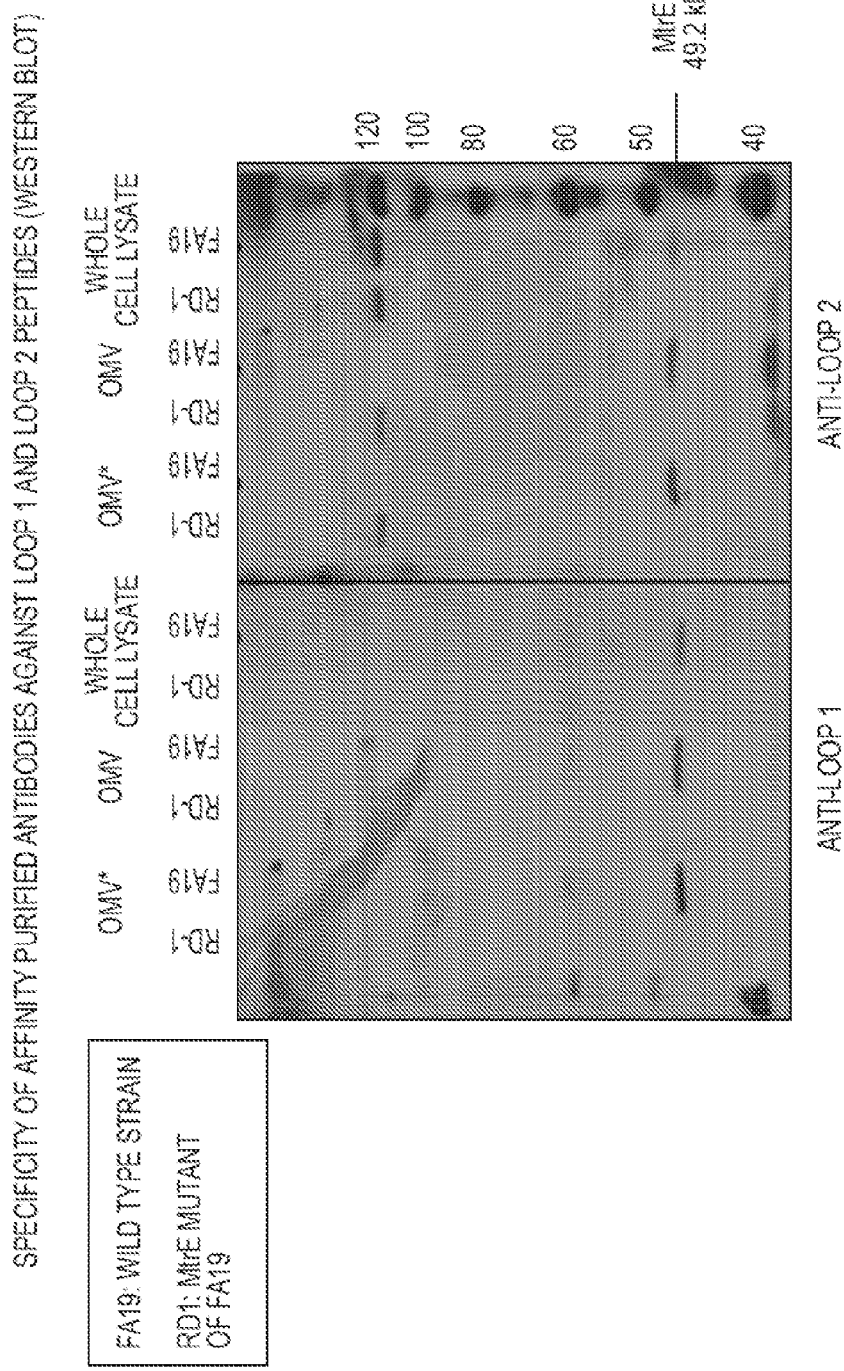
FIG. 3 depicts the specificity of antisera against MtrE peptides 112-118 (predicted loop 1) and 313-332 (predicted loop 2) of the MtrE protein as assessed by Western blot.
Figure 4:
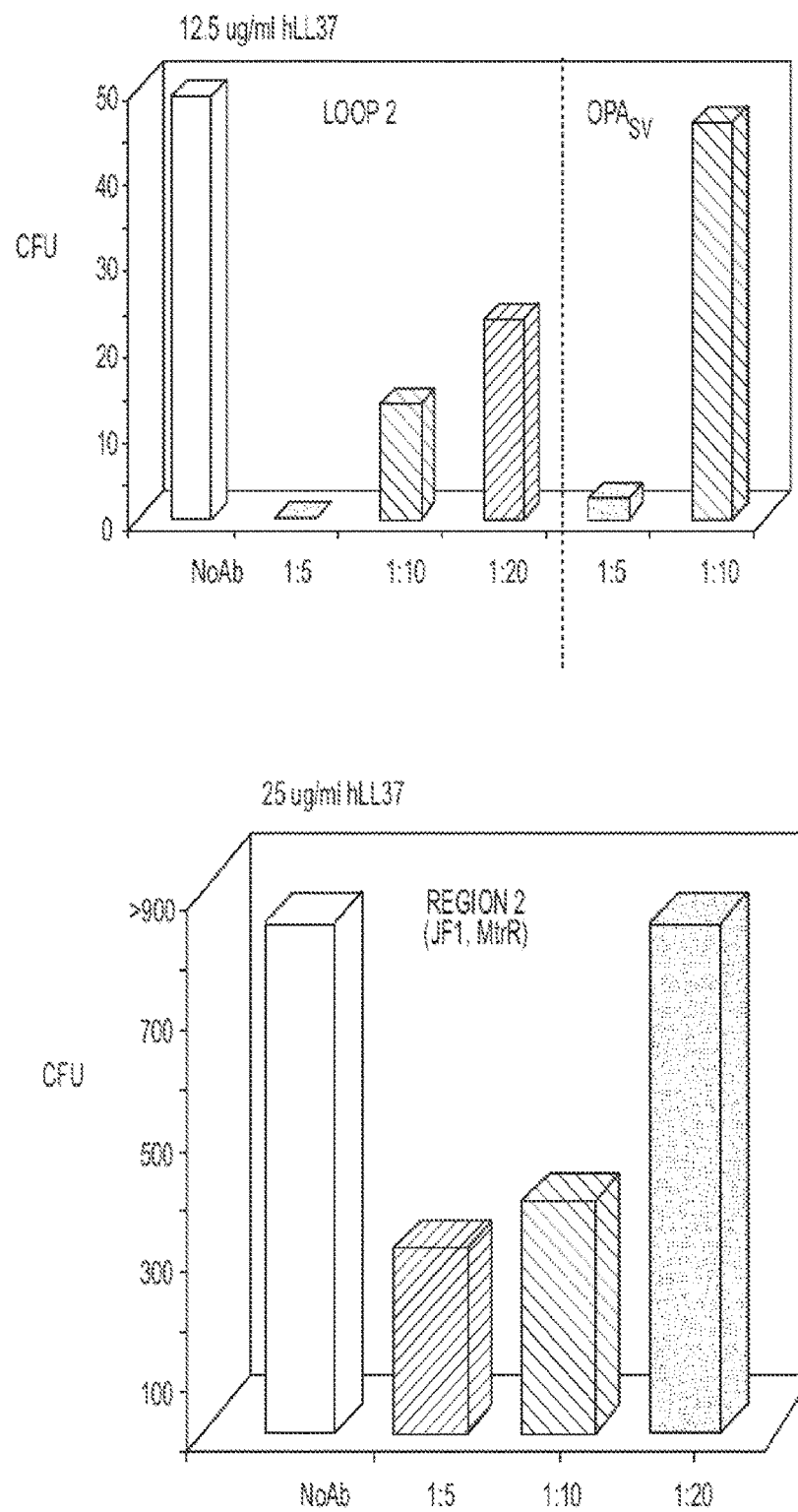
FIG. 4 depicts the capacity of affinity-purified antibodies against the predicted loop 2 peptide (MtrE 311-332) to inhibit pump function in wild type FA19 bacteria and strain JF-1, an over-producer of the MtrCDE active efflux pump. Antibodies to an unrelated antigen, $Opa_{SV}$, is not inhibitory at the same dilutions.
Figure 5:
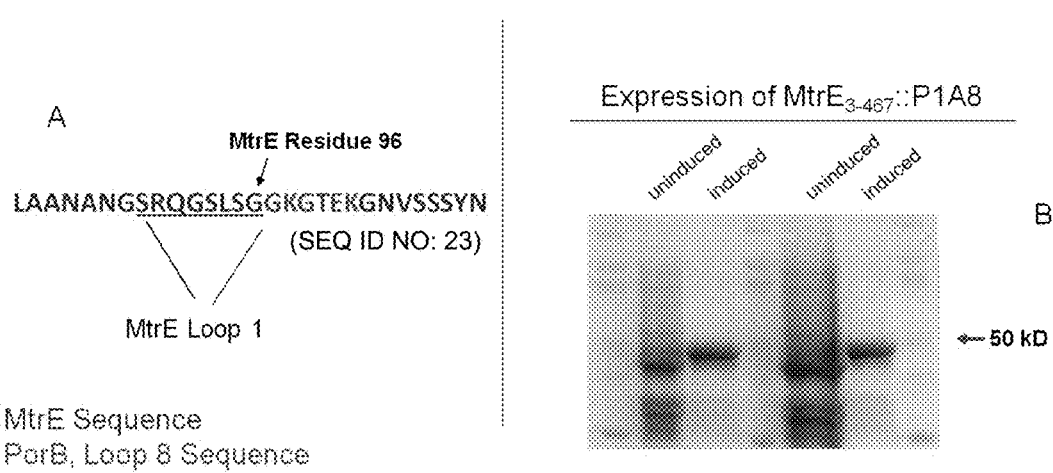
FIG. 5 depicts a construct of the present invention. The left panel (A) shows the resulting protein MtrE Loop 1 sequence from the MtrE-Porin Loop 8 fusion construct. On the right (B) uninduced and induced *E. coli* cultures were subjected to SDS-PAGE and stained with coomassie blue to show protein expression. A 50 kD protein is seen in the induced cultures and is indicative of the MtrE-Porin fusion protein. This band is absent in the uninduced cultures

The present application is directed to isolated MtrE peptides. As used herein, the terms "protein" and "peptide" are used interchangeably and simply used to denote at least a polymer, branched or unbranched, of amino acid residues. As used herein, the term "isolated," when used in conjunction with proteins and nucleic acids, is used to indicate that the proteins or nucleic acids are present in a form in which the protein does not naturally occur. For example, the MtrE protein in the present application is a protein that naturally occurs the in outer membrane of *N. gonorrhoeae*. Thus, an "isolated MtrE" protein is a protein that does not occur as part of the outer membrane of *N. gonorrhoeae*.

The isolated proteins of the present invention can occur in any in vitro or in vivo setting. For example, a cell containing a vector that encodes an MtrE protein of the present invention encompasses the term "isolated protein" as used herein. In another example, a bacterium other than *N. gonorrhoeae* expressing an MtrE protein in its outer membrane is also encompassed by the term "isolated protein" as used herein. Thus, an MtrE protein present in a cell that does not normally express MtrE, regardless of how it was introduced into the cell, is also encompassed within the term "isolated protein" as used herein.

However, a nucleic acid contained in a clone that is a member of a library, e.g., a genomic or cDNA library, that has not been isolated from other members of the library, e.g., in the form of a homogeneous solution containing the clone and other members of the library, or a chromosome isolated or removed from a cell or a cell lysate, e.g., a "chromosome spread," as in a karyotype, is not "isolated" for the purposes of the invention. As discussed further herein, isolated nucleic acid molecules according to the present invention may be produced naturally, recombinantly, or synthetically.

Of course, the isolated MtrE proteins or fragments described herein can be purified or substantially purified. As used herein, the term "purified" when used in reference to a protein or nucleic acid, means that the concentration of the molecule being purified has been increased relative to other molecules associated with it in its natural environment, or environment in which it was produced, found or synthesized. One of skill in the art would recognize that these "other molecules" might include proteins, nucleic acids, lipids and sugars but generally do not include water, solvents, buffers, and reagents added to maintain the integrity or facilitate the purification of the molecule being purified. For example, even if a protein is diluted with an aqueous solvent during affinity chromatography, the proteins are purified by this chromatography if other naturally associated molecules do not bind to the column and are separated from the subject proteins. According to this definition, a substance may be 5% or more, 10% or more, 20% or more, 30% or more, 40% or more, 50% or more, 60% or more, 70% or more, 80% or more, 90% or more, 95% or more, 98% or more, 99% or more, or 100% pure when considered relative to its contaminants.

The naturally occurring MtrE protein is part of the multiple transferable resistance efflux system (MtrCDE) present in *Neisseria gonorrhoeae* (*N. gonorrhoeae*). The term "*N. gonorrhoeae*" (or *Neisseria gonorrhoeae*) as used herein refers to any strain of the bacterium, including but not limited to the strains FA1090, FA19, MS11, and F62. The MtrE protein is the outer membrane protein portion of the efflux pump. The MtrE protein forms the outer membrane pore of the Gc MtrC-MtrD-MtrE (multiple transferable resistance) and FarA-FarB-MtrE (fatty acid resistance) multidrug resistance (MDR) efflux systems. MtrE functions with the inner membrane transporter and a periplasmic accessory protein to capture antimicrobial substrates and transport them through the periplasm to the external milieu. Clinical evidence suggests the MtrC-MtrD-MtrE active efflux pump system protects Gc from innate mucosal defenses. Natural substrates of the MtrC-MtrD-MtrE and FarA-FarB-MtrE systems found on urogenital or rectal mucosa include fatty acids, bile salts, antimicrobial peptides, and fecal lipids. The full length amino acid sequence of the *N. gonorrhoeae* MtrE, including the leader sequence, is presented herein as SEQ ID NO:1 below. The amino acid sequence of SEQ ID NO:1 contain the leader sequence at residues 1-20, such that the "mature MtrE protein" generally is amino acids 21-467 of SEQ ID NO:1, below. MtrE peptides 112-118 and 313-332, which correspond to surface-exposed loops 1 and 2, respectively and are indicated in the sequence below by single and double underlining, respectively.

```
                                         (SEQ ID NO: 1)
MNTTLKTTLT SVAAAFALSA CTMIPQYEQP KVEVAETFQN

DTSVSSIRAV DLGWHDYFAD PRLQKLIDIA LERNTSLRTA

VLNSEIYRKQ YMIERNNLLP TLAANANGSR QGSLSGGNVS

SSYNVGLGAA SYELDLFGRV RSSSEAALQG YFASVANRDA

AHLSLIATVA KAYFNERYAE EAMSLAQRVL KTREETYNAV

RIAVQGRRDF RRRPAPAEAL IESAKADYAH AARSREQARN

ALATLINRPI PEDLPAGLPL DKQFFVEKLP AGLSSEVLLD

RPDIRAAEHA LKQANANIGA ARAAFFPSIR LTGSVGTGSV

ELGGLFKSGT GVWAFAPSIT LPIFTWGTNK ANLDVAKLRQ

QAQIVAYESA VQSAFQDVAN ALAAREQLDK AYDALSKQSR

ASKEALRLVG LRYKHGVSGA LDLLDAERSS YSAEGAALSA

QLTRAENLAD LYKALGGGLK RDTQTGK
```

The present invention is directed to the full length MtrE protein, the mature MtrE protein, and fragments thereof. As used herein, the term "MtrE protein" (or "MtrE peptide") is used to mean proteins comprising the amino acid sequence of the mature MtrE, as defined by the amino acid sequence herein, as well as the orthologs, fragments, fusions and variants thereof that are disclosed herein. An MtrE protein as defined herein need not have the identical function of the wild-type MtrE protein and need not have any function. In one embodiment of the present invention, the MtrE proteins of the present invention possess at least partial functionality as wild-type, mature MtrE proteins.

The term "fragment," when used in connection with a protein, is used to mean a peptide that contains a sequence of contiguous amino acids taken from the full length or mature MtrE protein. In specific embodiments, the MtrE fragments of the present invention comprise alternatively consist of about 5 to 10, 10 to 15, 15 to 20, 20 to 25, 25 to 30, 30 to 35, 35 to 40, 40 to 45, 45 to 50, 50 to 55, 55 to 60, 60 to 65, 65 to 70, 70 to 75, 75 to 80, 80 to 85, 85 to 90, 90 to 95, 95 to 100, 100 to 105, 105 to 110, 110 to 115, 115 to 120, 120 to 125, 125 to 130, 130 to 135, 135 to 140, 140 to 145, 145 to 150, 150 to 155, 155 to 160, 160 to 165, 165 to 170, 170 to 175, 175 to 180, 180 to 185, 185 to 190, 190 to 195, 195 to 200, 200 to 205, 205 to 210, 210 to 215, 215 to 220, 220 to 225, 225 to 230, 230 to 235, 235 to 240, 240 to 245, 245 to 250, 250 to 255, 255 to 260, 260 to 265, 265 to 270, 270 to 275, 275 to 280, 280 to 285, 285 to 290, 290 to 295, 295 to 300, 300 to 305, 305 to 310, 310 to 315, 315 to 320, 320 to 325, 325 to 330, 330 to 335, 335 to 340, 340 to 345, 345 to 350, 350 to 355, 355 to 360, 360 to 365, 365 to 370, 370 to 375, 375 to 380, 380 to 385, 385 to 390, 390 to 395, 395 to 400, 400 to 405, 405 to 410, 410 to 415, 415 to 420, 420 to 425, 425 to 430, 430 to 435, 435 to 440, 440 to 445, 445 to 450, 450 to 455, 456, 457, 458, 459, 460, 461, 462, 463, 464, 465 or 466 contiguous amino acids of SEQ ID NO:1.

In specific embodiments, the invention provides isolated MtrE protein fragments with amino acid sequences comprising or alternatively consisting of amino acid residues 23-467 of SEQ ID NO:1, amino acid residues 23-155 of SEQ ID NO:1 or an amino acid residues 313-467 of SEQ ID NO:1. In other specific embodiments, the invention provides isolated MtrE peptides with amino acid sequences comprising or alternatively consisting of amino acid residues 112-118 of SEQ ID NO:1, and comprising or alternatively consisting of amino acid residues 313-332 of SEQ ID NO:1.

The invention also provides for variants of the MtrE proteins or fragments as described herein. Variants include but are not limited to naturally-occurring allelic variants, as well as mutants, variants or any other non-naturally occurring variants. In one embodiment, the variants cross-react with antibodies against an MtrE peptide of the present invention.

Allelic variants are very common in nature. For example, N. gonorrhoeae can be represented by a variety of strains or serovars that differ from each other by minor allelic variations. An allelic variant is an alternate form of a polypeptide that is often characterized as having a substitution, deletion, or addition of one or more amino acids that does not substantially alter the biological function of the polypeptide in cells in which it naturally occurs. For example, a polypeptide that fulfills the same biological function in different strains can have an amino acid sequence that may not be identical in each of the various strains of N. gonorrhoeae. Such an allelic variation may be equally reflected at the nucleic acid molecule level.

Nucleic acid molecules, e.g., DNA molecules, encoding allelic variants can easily be retrieved by the polymerase chain reaction (PCR) amplification of genomic bacterial DNA extracted by conventional methods. This involves the use of synthetic oligonucleotide primers matching upstream and downstream sequences of the 5' and 3' ends of the encoding domains. Typically, a primer can consist of 10 to 40, and even from 15 to 25 nucleotides, and it can often be advantageous to select primers containing G/C nucleotides in a proportion sufficient to ensure efficient hybridization.

In specific examples, the invention is directed to isolated variants of MtrE proteins comprising, or in the alternative consisting of an amino acid sequence that is at least 80% identical to residues 23-467 of SEQ ID NO:1, or an amino acid sequence that is at least 80% identical to residues 23-155 of SEQ ID NO:1 or an amino acid sequence that is at least 80% identical to residues 313-467 of SEQ ID NO:1. In additional embodiments, the invention is directed to isolated MtrE proteins that have amino acid sequences comprising, or in the alternative consisting of sequences, that are at least 85%, 86%, 87%, 88%, 89%, 90%, 91%, 92%, 93%, 94%, 95%, 96%, 97%, 98%, 99% and 100% identical to residues 23-467 of SEQ ID NO:1. In more embodiments, the invention is directed to isolated MtrE proteins that have amino acid sequences comprising, or in the alternative consisting of sequences, that are at least 85%, 86%, 87%, 88%, 89%, 90%, 91%, 92%, 93%, 94%, 95%, 96%, 97%, 98%, 99% A and 100% identical to residues 23-155 of SEQ ID NO:1. In still more embodiments, the invention is directed to isolated MtrE proteins that have amino acid sequences comprising, or in the alternative consisting of sequences, that are at least 85%, 86%, 87%, 88%, 89%, 90%, 91%, 92%, 93%, 94%, 95%, 96%, 97%, 98%, 99% and 100% identical to residues 313-467 of SEQ ID NO:1. In still more embodiments, the invention is directed to isolated MtrE proteins that have amino acid sequences comprising, or in the alternative consisting of sequences, that are at least 85%, 86%, 87%, 88%, 89%, 90%, 91%, 92%, 93%, 94%, 95%, 96%, 97%, 98%, 99% and 100% identical to residues 112-118 of SEQ ID NO:1. In still more embodiments, the invention is directed to isolated MtrE proteins that have amino acid sequences comprising, or in the alternative consisting of sequences, that are at least 85%, 86%, 87%, 88%, 89%, 90%, 91%, 92%, 93%, 94%, 95%, 96%, 97%, 98%, 99% and 100% identical to residues 313-332 of SEQ ID NO:1.

The MtrE proteins of the present invention may also comprise substitution variants. Substitution variants include those polypeptides wherein one or more amino acid residues of the MtrE proteins are removed and replaced with alternative residues. In one embodiment, the substitution variants of the present invention are conservative in nature. Conservative substitutions for this purpose may be defined as set out in the tables below, but in general are considered to be those substitutions that do not affect the overall function or three-dimensional structure of the protein. Amino acids can be classified according to physical properties and contribution to secondary and tertiary protein structure. A conservative substitution is recognized in the art as a substitution of one amino acid for another amino acid that has similar properties. Exemplary conservative substitutions are set out in below.

TABLE I

Conservative Substitutions

| Side Chain Characteristic | Amino Acid |
|---|---|
| Aliphatic | |
| Non-polar | Gly, Ala, Pro, Iso, Leu, Val |
| Polar-uncharged | Cys, Ser, Thr, Met, Asn, Gln |
| Polar-charged | Asp, Glu, Lys, Arg |
| Aromatic | His, Phe, Trp, Tyr |
| Other | Asn, Gln, Asp, Glu |

Alternatively, conservative amino acids can be grouped as described in Lehninger (1975) Biochemistry, Second Edition; Worth Publishers, pp. 71-77, as set forth below.

TABLE II

Conservative Substitutions

| Side Chain Characteristic | Amino Acid |
|---|---|
| Non-polar (hydrophobic) | |
| Aliphatic: | Ala, Leu, Iso, Val, Pro |
| Aromatic: | Phe, Trp |
| Sulfur-containing: | Met |
| Borderline: | Gly |
| Uncharged-polar | |
| Hydroxyl: | Ser, Thr, Tyr |
| Amides: | Asn, Gln |
| Sulfhydryl: | Cys |
| Borderline: | Gly |
| Positively Charged (Basic): | Lys, Arg, His |
| Negatively Charged (Acidic): | Asp, Glu |

And still other alternative, exemplary conservative substitutions are set out below.

TABLE III

Conservative Substitutions

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |

TABLE III-continued

Conservative Substitutions

| Original Residue | Exemplary Substitution |
|---|---|
| Gln (Q) | Asn |
| Glu (E) | Asp |
| His (H) | Asn, Gln, Lys, Arg |
| Ile (I) | Leu, Val, Met, Ala, Phe |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

The variants of the MtrE proteins and fragments thereof also include peptides comprising non-traditional amino acid residues. For example, the MtrE peptides and fragments thereof may include residues in the "D configuration" or amino acids that do not normally occur in proteins, such as but not limited to citrulline, ornithine, hypusine, selenocysteine α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, norleucine, norvaline, hydroxyproline, sarcosine, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, PNA's and amino acid analogs in general. Furthermore, the amino acid can be D or L isoform.

The fragments may or may not possess similar functionality as mature MtrE proteins. In one embodiment, the fragments of the present invention possess at least one known function of an MtrE protein. In another embodiment, the fragments of the present invention are antigenic. In another embodiment, the fragments of the present invention are immunogenic. For example, the MtrE-derived polypeptides of the invention may be immunologically cross-reactive and may be capable of eliciting in an animal an immune response to N. gonorrhoeae, N. gonorrhoeae infected cells or antigen presenting cells expressing N. gonorrhoeae antigens and/or are able to be bound by anti-MtrE antibodies. As used herein the term "antigenic" refers to a substance such as a peptide or nucleic acid to which an antibody or T-cell receptor specifically binds. The term "immunogenic" refers to a peptides ability to elicit at least a partial immune response, including but not limited to, production of neutralizing antibodies, recruitment of helper T cells, production cytokines and other inflammatory mediators, when administered to an organism. One of skill in the art readily understands the difference between an "antigenic response" and an "immunogenic response" as used herein.

The antigenicity and/or immunogenicity of the peptides or fragments described herein may or may not necessarily require the use of an adjuvant or combination of adjuvants such as, but not limited to, alum, aluminum phosphate, aluminum hydroxide, squalene, oil-based adjuvants, virosomes, QS21, MF59, interleukin 12 (IL-12), CpG, small molecule mast cell activator (MP7), TLR7 imidazoquinoline ligand 3M-019, resquimod (R848), N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dip-almitoyl-sn-glycero-3 hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80. Tables IV and V provide information on adjuvants that may be useful. Table IV shows possible adjuvants and their properties. These adjuvants may be used alone or in combination to test their ability to augment the immune response towards N. gonorrhoeae and MtrE. These adjuvants are defined by their ability to drive a Th1 or Th2 response. Table V shows adjuvants and adjuvant combinations of mice immunized with MtrE. The geometric mean of the final serum titer is shown. MtrE-specific antibody was detected via ELISA.

TABLE IV

| Adjuvant | Properties |
|---|---|
| CT | Potent mucosal adjuvant (Th2 response) |
| CpG | TLR 9 agonist (Th1 response) |
| MplA | TLR 4 agonist (Th1 response) |
| R 848 | TLR 7/8 agonist (Th1 response) |
| IL-12 | Pro-inflammatory cytokine (Th1 response) |
| CT + CpG | Th2 + Th1 response |
| CT + MplA | Th2 + Th1 response |
| CT + R 848 | Th2 + Th1 response |
| CT + IL-12 | Th2 + Th1 response |
| CpG + MplA | Th1 response |
| CpG + R 848 | Th1 response |
| CpG + Pam3CSK4 | Th1 response |

TABLE V

| Adjuvant | MtrE-Specific Titer |
|---|---|
| CT | 228,209 |
| CpG | 262,144 |
| R 848 | 32,768 |
| Pam3CSK4 | 155,871 |
| MPLA | 41,285 |
| CpG + R 848 | 131,072 |
| CpG + Pam3CSK4 | 92,681 |
| CpG + MPLA | 131,072 |

As used herein, the terms "correspond(s) to" and "corresponding to," as they relate to sequence alignment, are intended to mean enumerated positions within a reference protein, e.g., wild-type MtrE, and those positions in a modified MtrE that align with the positions on the reference protein. Thus, when the amino acid sequence of a subject protein is aligned with the amino acid sequence of a reference protein, the amino acids in the subject sequence that "correspond to" certain enumerated positions of the reference sequence are those that align with these positions of the reference sequence, but are not necessarily in these exact numerical positions of the reference sequence. Methods for aligning sequences for determining corresponding amino acids between sequences are described herein.

The amino acid residues of the MtrE proteins of the present invention may or may not be modified such as, but not limited to, addition of functional or non-functional groups such a but not limited to, acetyl groups, hydroxyl groups, carboxyl groups, carbohydrate groups (glycosylation), phosphate groups and lipid groups to name a few. Any of numerous chemical modifications may be carried out by known techniques, including but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.

The MtrE proteins of the present invention may or may not contain additional elements that, for example, may include but are not limited to regions to facilitate purification. For example, "histidine tags" ("his tags") or "lysine tags" may be appended or "fused" to the MtrE proteins to create "MtrE fusion proteins." Examples of histidine tags include, but are not limited to hexaH, heptaH and hexaHN. Examples of lysine tags include, but are not limited to pentaL, heptaL and FLAG. Such regions may be removed prior to final preparation of the MtrE proteins. Other examples of a second fusion peptide include, but are not limited to, glutathione S-transferase (GST) and alkaline phosphatase (AP).

The addition of peptide moieties to MtrE proteins, whether to engender secretion or excretion, to improve stability and to facilitate purification or translocation, among others, is a familiar and routine technique in the art and may include modifying amino acids at the terminus to accommodate the tags. For example the N-terminus amino acid may be modified to, for example, arginine and/or serine to accommodate a tag. Of course, the amino acid residues of the C-terminus may also be modified to accommodate tags. One particularly useful fusion protein comprises a heterologous region from immunoglobulin that can be used solubilize proteins.

Other types of fusion proteins provided by the present invention include but are not limited to, fusions with secretion signals and other heterologous functional regions. Thus, for instance, a region of additional amino acids, particularly charged amino acids, may be added to the N-terminus of the MtrE proteins to improve stability and persistence in the host cell, during purification or during subsequent handling and storage.

Another particular example of fusion polypeptides of the invention includes an MtrE polypeptide, fragment or variant thereof fused to a polypeptide having adjuvant activity, such as the subunit B of either cholera toxin or *E. coli* heat labile toxin. Another particular example of a fusion polypeptide encompassed by the invention includes an MtrE polypeptide fused to a cytokine, such as, but not limited to, IL-2, IL-4, IL-10, IL-12, or interferon. An MtrE polypeptide of the invention can be fused to the N- or C-terminal end of a polypeptide having adjuvant activity. Alternatively, an MtrE polypeptide of the invention can be fused within the amino acid sequence of the polypeptide having adjuvant activity.

Also, in one embodiment, the MtrE polypeptides, and fusions thereof, of may comprise sequences that form one or more epitopes of a native *N. gonorrhoeae* MtrE polypeptide that elicit bactericidal or opsonizing antibodies and/or T-cells. Such MtrE polypeptides may be identified by their ability to generate antibodies and/or T-cells that kill cells infected with *N. gonorrhoeae* cells.

The MtrE proteins and MtrE fusion proteins of the current invention can be recovered and purified from recombinant cell cultures by well-known methods including, but not limited to, ammonium sulfate or ethanol precipitation, acid extraction, anion or cation exchange chromatography, phosphocellulose chromatography, hydrophobic interaction chromatography, affinity chromatography, e.g., immobilized metal affinity chromatography (IMAC), hydroxylapatite chromatography and lectin chromatography. High performance liquid chromatography ("HPLC") may also be employed for purification. Well-known techniques for refolding protein may be employed to regenerate active conformation when the MtrE protein is denatured during isolation and/or purification.

If desired, the individual amino acid sequences of the components of the fusion proteins can be produced and joined by a linker. Suitable peptide linker sequences may be chosen based on the following factors: (1) their ability to adopt a flexible extended conformation, (2) their ability to adopt a secondary structure that could interact with functional epitopes of the first and second polypeptides, (3) the lack of hydrophobic or charged residues that might react with the polypeptide functional epitopes, (4) the ability to increase solubility, and (5) the ability to increase sensitivity to processing by antigen-presenting cells. Such linkers can be any amino acid sequence or other appropriate link or joining agent.

Linkers useful in the invention include linkers comprising a charged amino acid pair such as KK or RR, linkers sensitive to cathepsin and/or other trypsin-like enzymes, thrombin or Factor $X_a$, or linkers which result in an increase in solubility of the polypeptide. Specific examples of linkers include those linkers that contain Gly, Asn and Ser residues. Amino acid sequences which may be usefully employed as linkers include those disclosed in Maratea et al., *Gene* 40:39-46 (1985), Murphy et al., *Proc. Nat. Acad Sci USA*, 83:8258-8562 (1986), U.S. Pat. Nos. 4,935,233 and 4,751,180, all of which are incorporated by reference. The linker sequence may be from 1 to about 150 amino acids in length or even longer.

The MtrE proteins and fusions thereof include but are not limited to products of chemical synthetic procedures and products produced by recombinant techniques from a prokaryotic or eukaryotic host, including, for example, bacterial, yeast, higher plant, insect and mammalian cells. Depending upon the host employed in a recombinant production procedure, the MtrE proteins and fusions thereof of the present invention may be glycosylated or may be non-glycosylated. In addition, the MtrE proteins and fusions thereof of the present invention may also include an initial modified methionine residue, in some cases as a result of host-mediated processes.

The invention is not limited to the source of the MtrE proteins or fusions thereof. One source, for example, is a protein preparation from a gene expression system (such as *E. coli*) engineered to express a cloned sequence encoding an MtrE polypeptide or fusion thereof.

The MtrE proteins and/or fusions thereof can be isolated and purified from the source material using any biochemical technique and approach well known to those skilled in the art. In one approach, *N. gonorrhoeae* cellular envelope is obtained by standard techniques and inner membrane, periplasmic and outer membrane proteins are solubilized using a solubilizing compound such as a detergent or hypotonic solution. One useful detergent solution is one containing octyl glucopyranoside (OG), sarkosyl n-Dodecyl-β-D-Maltopyranosid or TRITON X100™ (t-octyl phenoxy-polyethoxy-ethanol). One example of a solubilizing hypotonic solution is one containing LiCl, and the MtrE polypeptide may be in the solubilized fraction. Cellular debris and insoluble material in the extract are separated and removed, for example by centrifugation. The polypeptides in the extract are concentrated, incubated in SDS-containing Laemmli gel sample buffer at 100° C. for 5 minutes and then fractionated by electrophoresis in a denaturing sodium dodecylsulfate (SDS) polyacrylamide gel from about 6% to about 12%, with or without a reducing agent. The band or fraction identified as a MtrE polypeptide may then be purified directly from the fraction or gel slice containing the MtrE polypeptide.

Another method of purifying MtrE polypeptide or fusion thereof is by affinity chromatography using anti-MtrE antibodies. The affinity chromatography may be carried out using either polyclonal or monoclonal anti-MtrE antibodies. The antibodies can be covalently linked to agarose gels activated by cyanogen bromide or succinamide esters (Affi-Gel, BioRad, Inc.) or by other methods known to those skilled in the art. The protein extract can be loaded on the top of the gel and can be left in contact with the gel for a period of time and under standard reaction conditions sufficient for MtrE polypeptide to bind to the antibody. The solid support may be a material used in a chromatographic column. The affinity gel is washed to remove other proteins and cell materials not bound by the anti-MtrE antibody. The MtrE polypeptide is then removed from the antibody to recover the MtrE polypeptide in isolated or purified form.

An MtrE polypeptide and/or fusion thereof can be produced by chemical and/or enzymatic cleavage or degradation of an isolated or purified MtrE polypeptide. An MtrE polypeptide can also be chemically synthesized based on the known amino acid sequence of the MtrE polypeptide and, in the case of a chimeric or fusion polypeptide, the amino acid sequence of the heterologous polypeptide, by methods well known in the art.

An MtrE polypeptide and/or fusion thereof can also be produced in a gene expression system expressing a recombinant nucleic acid construct comprising a sequence encoding an MtrE polypeptide of the present invention. The nucleotide sequences encoding polypeptides of the invention may be synthesized, and/or cloned, and expressed according to techniques well known to those skilled in the art. See, for example, Sambrook, et al., 1989, *Molecular Cloning, A Laboratory Manual*, Vols. 1-3, Cold Spring Harbor Press, NY, which is incorporated by reference in its entirety.

If desirable, the MtrE polypeptides of the invention may be further purified using standard protein or peptide purification techniques including but not limited to, electrophoresis, centrifugation, gel filtration, precipitation, dialysis, chromatography (including ion exchange chromatography, affinity chromatography, immunoadsorbent affinity chromatography, dye-binding chromatography, size exclusion chromatography, hydroxyapatite chromatography, reverse-phase high performance liquid chromatography, and gel permeation high performance liquid chromatography), isoelectric focusing, and variations and combinations thereof.

One or more of these techniques may be employed sequentially in a procedure designed to isolate and/or purify the MtrE polypeptides of the present invention according to its/their physical or chemical characteristics. These characteristics include the hydrophobicity, charge, binding capability, and molecular weight of the proteins. The various fractions of materials obtained after each technique are tested for binding to, for example, the anti-MtrE antibodies or for functional activity. Those fractions showing such test activity are then pooled and subjected to the next technique in the sequential procedure, and the new fractions are tested again. The process can be repeated as often as desired.

The present invention provides antibodies that specifically bind an MtrE polypeptide and/or an epitope on *N. gonorrhoeae*. For the production of such antibodies, isolated or purified preparations of an MtrE polypeptide of the present invention can be used as an immunogen in an immunogenic composition. The same immunogen can be used to immunize mice for the production of hybridoma lines that produce monoclonal anti-MtrE antibodies. In particular embodiments, the immunogen is an isolated or purified MtrE polypeptide of the present invention.

In other embodiments, the MtrE polypeptides of the present invention are used as immunogens. The peptides may be produced by protease digestion, chemical cleavage of isolated or purified MtrE polypeptide, chemical synthesis or by recombinant expression, after which they are then isolated or purified. Such isolated or purified peptides can be used directly as immunogens. In particular embodiments, useful peptide fragments are 8 or more amino acids in length.

Useful immunogens may also comprise such MtrE peptides conjugated to a carrier molecule, such as a carrier protein. Carrier proteins may be any commonly used in immunology, include, but are not limited to, bovine serum albumin (BSA), chicken albumin, keyhole limpet hemocyanin (KLH), tetanus toxoid, synthetic T cell epitopes and the like.

In one embodiment, the anti-MtrE antibodies are monoclonal antibodies. In another embodiment, the anti-MtrE antibodies are polyclonal antibodies.

In further embodiments, useful immunogens for eliciting antibodies of the invention comprise mixtures of two or more of any of the above-mentioned individual immunogens.

Immunization of animals with the immunogens described herein, for example in humans, rabbits, rats, ferrets, mice, sheep, goats, cows or horses, can be performed following procedures well known to those skilled in the art, for purposes of obtaining antisera containing polyclonal antibodies or hybridoma lines secreting monoclonal antibodies.

Monoclonal antibodies can be prepared by standard techniques, given the teachings contained herein. Such techniques are disclosed, for example, in U.S. Pat. Nos. 4,271,145 and 4,196,265, which are incorporated by reference. Briefly, an animal is immunized with the immunogen. Hybridomas are prepared by fusing spleen cells from the immunized animal with myeloma cells. The fusion products are screened for those producing antibodies that bind to the immunogen. The positive hybridomas clones are isolated, and the monoclonal antibodies are recovered from those clones.

Immunization regimens for production of both polyclonal and monoclonal antibodies are well known in the art. The immunogen may be injected by any of a number of routes, including subcutaneous, intravenous, intraperitoneal, intradermal, intramuscular, mucosal (e.g., nasal, vaginal, rectal), or a combination of these. The immunogen may be injected in soluble form, aggregate form, attached to a physical carrier, or mixed with an adjuvant, using methods and materials well known in the art. The antisera and antibodies may be purified using column chromatography methods well known to those of skill in the art.

The antibodies may also be used as probes for identifying clones in expression libraries that have or may have inserts encoding one or more MtrE polypeptides described herein. The antibodies or MtrE polypeptides may also be used in immunoassays, e.g., ELISA, RIA, Western Blots, to specifically detect and/or quantitate *N. gonorrhoeae* or anti-*N. gonorrhoeae* antibody in biological specimens. The anti-MtrE antibodies of the invention specifically bind it MtrE from *N. gonorrhoeae* and can be used to diagnose *N. gonorrhoeae* infections.

The antibodies of the invention, including but not limited to those that are cytotoxic, cytostatic, or neutralizing, may also be used in passive immunization to prevent or attenuate *N. gonorrhoeae* infections of animals, including humans. As used herein, a cytotoxic antibody is one that enhances opsonization and/or complement killing of the bacterium bound by the antibody. As used herein, neutralizing antibody is one that reduces the infectivity of the *N. gonorrhoeae* and/or blocks binding of *N. gonorrhoeae* to a target cell. An effective concentration of polyclonal or monoclonal antibodies raised against the immunogens of the invention may be administered to a host to achieve such effects. The exact concentration of the antibodies administered will vary according to each specific antibody preparation, but may be determined using standard techniques well known to those of ordinary skill in the art. Administration of the antibodies may be accomplished using a variety of techniques, including but not limited to those described herein.

Another aspect of the invention is directed to antisera raised against an antigenic or immunogenic composition of the invention, and antibodies present in the antisera that specifically bind an MtrE protein of the present invention. In one specific embodiment, the antibodies or antibody fragments described herein bind to peptides with an amino acid sequence of SEQ ID NO:2 or SEQ ID NO:3.

The term "antibodies" is intended to include all forms, such as but not limited to polyclonal, monoclonal, purified IgG, IgM, or IgA antibodies and fragments thereof, including but not limited to antigen binding fragments such as Fv, single chain Fv (scFv), F(ab)$_2$, Fab, and F(ab)' fragments, single chain antibodies as disclosed in U.S. Pat. No. 4,946, 778 (incorporated by reference), as well as complementary determining regions (CDR) as disclosed in Verhoeyen and Winter, in Molecular Immunology 2ed., by B. D. Hames and D. M. Glover, IRL Press, Oxford University Press, 1996, at pp. 283-325 (incorporated by reference) etc.

A further aspect of the invention are chimeric or humanized antibodies (Morrison et al., 1984, Proc. Nat'l Acad. Sci. USA 81:6851; Reichmann et al. Nature 332:323: U.S. Pat. Nos. 5,225,539; 5,585,089; and U.S. Pat. No. 5,530,101; Neuberger et al., 1984, Nature 81:6851 Riechmann et al., 1988, Nature 332:323; U.S. Pat. Nos. 5,225,539; 5,585,089; and 5,530,101, all of which are incorporated by reference) in which one or more of the antigen binding regions of the anti-MtrE antibody is introduced into the framework region of a heterologous (e.g. human) antibody. The chimeric or humanized antibodies of the invention are less antigenic in humans than non-human antibodies but have the desired antigen binding and other activities, including but not limited to neutralizing activity, cytotoxic activity, opsonizing activity or protective activity.

In one aspect of the invention, the antibodies of the invention are human antibodies. Human antibodies may be isolated, for example, from human immunoglobulin libraries (see, e.g., PCT publications WO 98/46645, WO 98/50433, WO 98/24893, WO 98/16054, WO 96/34096, WO 96/33735, and WO 91/10741, all of which are incorporated by reference) by, for example, phage display techniques (see, e.g., Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427, 908; 5,750,753; 5,821,047; 5,571,698; 5,427,908; 5,516, 637; 5,780,225; 5,658,727; 5,733,743 and 5,969,108; each of which is incorporated herein by reference in its entirety. Human antibodies may also be generated from animals transgenic for one or more human immunoglobulin and that do not express endogenous immunoglobulins, see, e.g., U.S. Pat. No. 5,939,598, which is incorporated by reference.

A further aspect of the invention is T-cells specific for *N. gonorrhoeae, N. gonorrhoeae* infected cells or antigen presenting cells displaying *N. gonorrhoeae* antigens. T-cell preparations enriched for T-cells specific for the MtrE polypeptides of the present invention can be produced or isolated by methods known in the art The invention also provides polynucleotides that code for the isolated MtrE proteins disclosed herein. The nucleic acids of the invention can be DNA or RNA, for example, mRNA. The nucleic acid molecules can be double-stranded or single-stranded; single stranded RNA or DNA can be the coding, or sense, strand or the non-coding, or antisense, strand. In particular, the nucleic acids may encode any of the MtrE proteins disclosed herein, as well as variants thereof. Of course, the nucleic acids of the present invention may encode additional elements, such as his tags and the like. For example, the nucleic acids of the invention would include those that encode any of the MtrE proteins and variants thereof that are also contain a glutathione-S-transferase (GST) fusion protein, poly-histidine (e.g., Hiss), poly-HN, poly-lysine, etc. If desired, the nucleotide sequences can include additional non-coding sequences such as non-coding 3' and 5' sequences (including regulatory sequences, for example).

In another specific embodiment, the invention provides nucleic acids that are hybridizable to a nucleic acid encoding an MtrE polypeptide of the present invention. Various other stringency conditions that promote nucleic acid hybridization can be used. For example, hybridization in 6×SSC at about 45° C., followed by washing in 2×SSC at 50° C. may be used. Alternatively, the salt concentration in the wash step can range from low stringency of about 5×SSC at 50° C., to moderate stringency of about 2×SSC at 50° C., to high stringency of about 0.2×SSC at 50° C. In addition, the temperature of the wash step can be increased from low stringency conditions at room temperature, to moderately stringent conditions at about 42° C., to high stringency conditions at about 65° C. Other conditions include, but are not limited to, hybridizing at 68° C. in 0.5M NaHPO$_4$ (pH7.2)/1 mM EDTA/7% SDS, or hybridization in 50% formamide/0.25M NaHPO$_4$ (pH 7.2)/0.25 M NaCl/1 mM EDTA/7% SDS; followed by washing in 40 mM NaHPO$_4$ (pH 7.2)/1 mM EDTA/5% SDS at 42° C. or in 40 mM NaHPO$_4$ (pH7.2)/1 mM EDTA/1% SDS at 50° C. Both temperature and salt may be varied, or alternatively, one or the other variable may remain constant while the other is changed.

Low, moderate and high stringency conditions are well known to those of skill in the art, and will vary predictably depending on the base composition of the particular nucleic acid sequence and on the specific organism from which the nucleic acid sequence is derived. For guidance regarding such conditions see, for example, Sambrook et al., 1989, *Molecular Cloning, A Laboratory Manual*, Second Edition, Cold Spring Harbor Press, N.Y and Ausubel et al., 1989, *Current Protocols in Molecular Biology*, Green Publishing Associates and Wiley Interscience, N.Y.

Nucleic acids encoding MtrE polypeptides of the present invention may be produced by methods well known in the art. In one aspect, nucleic acids encoding the MtrE polypeptides can be derived from MtrE polypeptide coding sequences by recombinant DNA methods known in the art. For example, the coding sequence of an MtrE polypeptide may be altered creating amino acid substitutions that will not affect the immunogenicity of the MtrE polypeptide or which may improve its immunogenicity, such as conservative or semi-conservative substitutions as described above. Various methods may be used, including but not limited to, oligo-nucleotide directed, site specific mutagenesis. This and other techniques known in the art may be used to create single or multiple mutations, such as replacements, insertions, deletions, and transpositions, for example, as described in Botstein and Shortle, 1985, Science 229:1193-1210, which is incorporated by reference.

In one embodiment, the nucleic acids encoding the MtrE proteins are synthetic nucleic acids in which the codons have been optimized for increased expression in the host cell in which it is produced. The degeneracy of the genetic code permits variations of the nucleotide sequence, while still producing a polypeptide having the identical amino acid sequence as the polypeptide encoded by the native DNA sequence. The frequency of individual synonymous codons for amino acids varies widely from genome to genome among eukaryotes and prokaryotes. These differences in codon choice patterns appear to contribute to the overall expression levels of individual genes by modulating peptide elongation rates. For this reason it may be desirable and useful to design nucleic acid molecules intended for a particular expression system where the codon frequencies reflect the tRNA frequencies of the host cell or organism in which the protein is expressed. Native codons are exchanged for codons of highly expressed genes in the host cells. For instance, the nucleic acid molecule can be optimized for expression of the encoded protein in bacterial cells (e.g., *E. coli*), yeast (e.g., *Pichia*), insect cells (e.g., *Drosophila*), or mammalian cells or animals (e.g., human, sheep, bovine or mouse cells or animals).

Restriction enzyme sites critical for gene synthesis and DNA manipulation are preserved or destroyed to facilitate nucleic acid and vector construction and expression of the encoded protein. In constructing the synthetic genes of the invention it may be desirable to avoid CpG sequences as these sequences may cause gene silencing. The codon optimized sequence can be synthesized and assembled and inserted into an appropriate expression vector using conventional techniques well known to those of skill in the art.

In one particular embodiment, a synthetic nucleic acid encoding an MtrE protein of the present invention comprises at least one codon substitution in which non-preferred or less preferred codon in the natural gene encoding the protein has been replaced by a preferred codon encoding the same amino acid. For instance in humans the preferred codons are: Ala (GCC); Arg (CGC); Asn (AAC); Asp (GAC); Cys (TGC); Gln (CAG); Gly (GGC); His (CAC); Ile (ATC); Leu (CTG); Lys (AAG); Pro(CCC); Phe (TTC); Ser (AGC); Thr (ACC); Tyr (TAC); and Val (GTG). Less preferred codons are: Gly (GGG); Ile (ATT); Leu (CTC); Ser (TCC); Val (GTC); and Arg (AGG). In general, the degree of preference of a particular codon is indicated by the prevalence of the codon in highly expressed genes. Replacing a codon with another codon that is more prevalent in highly expressed human genes will generally increase expression of the gene in mammalian cells. Accordingly, the invention includes replacing a less preferred codon with a preferred codon as well as replacing a non-preferred codon with a preferred or less preferred codon.

Further, nucleic acids containing the MtrE polypeptide coding sequences may be truncated by restriction enzyme or exonuclease digestions. Heterologous coding sequences may be added to the MtrE polypeptide coding sequences by ligation or PCR amplification. Moreover, DNA encoding the whole or a part of MtrE polypeptide of the present invention may be synthesized chemically or using PCR amplification based on the known or deduced amino acid sequence of the MtrE polypeptide and any desired alterations to that sequence.

The identified and isolated DNA encoding the MtrE polypeptides of the present invention can be inserted into an appropriate cloning vector. A large number of vector-host systems known in the art may be used. The term "host" or "host cell" as used herein refers to either in vivo in an animal or in vitro in mammalian cell cultures.

The present invention also comprises vectors containing the nucleic acids encoding the MtrE proteins of the present invention. As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. An expression vector is one into which a desired DNA sequence may be inserted by restriction and ligation such that it is operably joined to regulatory sequences and may be expressed as an RNA transcript. Vectors may further contain one or more marker sequences suitable for use in the identification and selection of cells which have been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques. Examples of vectors include but are not limited to those capable of autonomous replication and expression of the structural gene products present in the DNA segments to which they are operably joined.

In certain respects, the vectors to be used are those for expression of polynucleotides and proteins of the present invention. Generally, such vectors comprise cis-acting control regions effective for expression in a host operatively linked to the polynucleotide to be expressed. Appropriate trans-acting factors are supplied by the host, supplied by a complementing vector or supplied by the vector itself upon introduction into the host.

A great variety of expression vectors can be used to express the proteins of the invention. Such vectors include chromosomal, episomal and virus-derived vectors, e.g., vectors derived from bacterial plasmids, from bacteriophage, from yeast episomes, from yeast chromosomal elements, from viruses such as adeno-associated virus, lentivirus, baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. All may be used for expression in accordance with this aspect of the present invention. Generally, any vector suitable to maintain, propagate or the fusion proteins in a host may be used for expression in this regard.

The DNA sequence in the expression vector is generally operably linked to appropriate expression control sequence(s) including, for instance, a promoter to direct mRNA transcription. Representatives of such promoters include, but are not limited to, the phage lambda PL promoter, the *E. coli* lac, trp and tac promoters, HIV promoters, the SV40 early and late promoters and promoters of retroviral LTRs, to name just a few of the well-known promoters. In general, expression constructs will contain sites for transcription, initiation and termination and, in the transcribed region, a ribosome binding site for translation. The coding portion of the mature transcripts expressed by the constructs will include a translation initiating AUG at the beginning and a termination codon (UAA, UGA or UAG) appropriately positioned at the end of the polypeptide to be translated.

In addition, the constructs may contain control regions that regulate, as well as engender expression. Generally, such regions will operate by controlling transcription, such as repressor binding sites and enhancers, among others.

Vectors for propagation and expression generally will include selectable markers. Such markers also may be suitable for amplification or the vectors may contain additional markers for this purpose. In this regard, the expression vectors may contain one or more selectable marker genes to provide a phenotypic trait for selection of transformed host cells. Preferred markers include dihydrofolate reductase or neomycin resistance for eukaryotic cell culture, and tetracycline, kanamycin or ampicillin resistance genes for culturing *E. coli* and other bacteria.

Promoter/enhancer elements which may be used to control expression of inserted sequences include, but are not limited to the SV40 early promoter region (Bernoist and Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42) for expression in animal cells, the promoters of lactamase (Villa-Kamaroff et al., 1978, Proc. Natl. Acad. Sci. U.S.A. 75:3727-3731), tac (DeBoer et al., 1983, Proc. Natl. Acad. Sci. U.S.A. 80:21-25), or trc for expression in bacterial cells (see also "Useful proteins from recombinant bacteria" in Scientific American, 1980, 242:74-94), the nopaline synthetase promoter region or the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115-120) for expression in plant cells; Gal4 promoter, the ADC (alcohol dehydrogenase) promoter, PGK (phosphoglycerol kinase) promoter, alkaline phosphatase promoter for expression in yeast or other fungi.

Depending on the host-vector system utilized, any one of a number of suitable transcription and translation elements may be used. In one embodiment, a fusion protein comprising an MtrE polypeptide of the present invention and a pre and/or pro sequence of the host cell is expressed. In other embodiments, a fusion protein comprising an MtrE protein of the present invention fused with, for example, an affinity purification peptide, including but not limited to, maltose binding protein, glutathione-S-transferase, thioredoxin or histidine tag, is expressed. In additional embodiments, a chimeric protein comprising an MtrE polypeptide of the present invention and a useful immunogenic peptide or protein is expressed.

Any method known in the art for inserting DNA fragments into a vector may be used to construct expression vectors containing an MtrE polypeptide encoding nucleic acid molecule comprising appropriate transcriptional/translational control signals and the polypeptide coding sequences. These methods may include in vitro recombinant DNA and synthetic techniques and in vivo recombination.

Methods of introducing exogenous DNA into yeast hosts include either the transformation of spheroplasts or of intact yeast cells treated with alkali cations. Transformation procedures usually vary with the yeast species to be transformed. See e.g., Kurtz et al. (1986) Mol. Cell. Biol. 6:142; Kunze et al. (1985) J. Basic Microbiol. 25:141; for *Candida*, Gleeson et al. (1986) J. Gen. Microbiol. 132:3459; Roggenkamp et al. (1986) Mol. Gen. Genet. 202:302; for *Hansenula*; Das et al. (1984) J. Bacteriol. 158:1165; De Louvencourt et al. (1983) J. Bacteriol. 154:1165; Van den Berg et al. (1990) Bio/Technology 8:135; for *Kluyveromyces*; Cregg et al. (1985) Mol. Cell. Biol. 5:3376; Kunze et al. (1985) J. Basic Microbiol. 25:141; U.S. Pat. Nos. 4,837,148 and 4,929,555; for *Pichia*; Hinnen et al. (1978) Proc. Natl. Acad. Sci. USA 75; 1929; Ito et al. (1983) J. Bacteriol. 153:163; for *Saccharomyces*; Beach et al. (1981) Nature 300:706; for *Schizosaccharomyces*; Davidow et al. (1985) Curr. Genet. 10:39.

Commercially available vectors for expressing heterologous proteins in bacterial hosts include but are not limited to pZERO, pTrc99A, pUC19, pUC18, pKK223-3, pEX1, pCAL, pET, pSPUTK, pTrxFus, pFastBac, pThioHis, pTrcHis, pTrcHis2, and pLEx. For example, the phage in lambda GEM™-11 may be utilized in making recombinant phage vectors which can be used to transform host cells, such as *E. coli* LE392. In a preferred embodiment, the vector is pQE30 or pBAD/ThioE, which can be used transform host cells, such as *E. coli*.

Expression and transformation vectors for transformation into many yeast strains are available. For example, expression vectors have been developed for, the following yeasts: *Candida albicans*, Kurtz, et al. (1986) Mol. Cell. Biol. 6:142; *Candida maltosa*, Kunze, et al. (1985) J. Basic Microbiol. 25:141; *Hansenula polymorpha*, Gleeson, et al. (1986) J. Gen. Microbiol. 132:3459; Roggenkamp et al. (1986) Mol. Gen. Genet. 202:302; *Kluyveromyces fragilis*, Das, et al. (1984) J. Bacteriol. 158:1165; *Kluyveromyces lactis*, De Louvencourt et al. (1983) J. Bacteriol. 154:737; Van den Berg, et al. (1990) Bio/Technology 8:135; *Pichia quillerimondii*, Kunze et al. (1985) J. Basic Microbiol. 25:141; *Pichia pastoris*, Cregg, et al. (1985) Mol. Cell. Biol. 5:3376, U.S. Pat. Nos. 4,837,148 and 4,929,555; *Saccharomyces cerevisiae*, Hinnen et al. (1978) Proc. Natl. Acad. Sci. USA 75:1929, Ito et al. (1983) J. Bacteriol. 153:163; *Schizosaccharomyces pombe*, Beach et al. (1981) Nature 300:706; and *Yarrowia lipolytica*, Davidow, et al. (1985) Curr. Genet. 10:380-471, Gaillardin, et al. (1985) Curr. Genet. 10:49.

The invention also provides for host cells comprising the nucleic acids and vectors described herein. A variety of host-vector systems may be utilized to express the polypeptide-coding sequence. These include but are not limited to mammalian cell systems infected with virus (e.g., vaccinia virus, adenoviris, etc.); insect cell systems infected with virus (e.g., baculovirus); microorganisms such as yeast containing yeast vectors, or bacteria transformed with bacteriophage DNA, plasmid DNA, or cosmid DNA, plant cells or transgenic plants.

Hosts that are appropriate for expression of nucleic acid molecules of the present invention, fragments, analogues or variants thereof, may include *E. coli, Bacillus* species, *Haemophilus*, fungi, yeast, such as *Saccharomyces, Pichia, Bordetella*, or *Candida*, or the baculovirus expression system.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered MtrE polypeptides may be controlled. Furthermore, different host cells have characteristic and specific mechanisms for the translational and post-translational processing and modification of proteins. Appropriate cell lines or host systems can be chosen to ensure the desired modification and processing of the foreign protein expressed.

Once a suitable host system and growth conditions are established, recombinant expression vectors can be propagated and prepared in quantity. Upon expression, a recombinant polypeptide of the invention is produced and can be recovered in a substantially purified from the cell paste, the cell extract or from the supernatant after centrifugation of the recombinant cell culture using techniques well known in the art.

For instance, the recombinant polypeptide can be purified by antibody-based affinity purification, preparative gel electrophoresis, or affinity purification using tags (e.g., 6× histidine tag) included in the recombinant polypeptide.

The present invention is also directed to methods of producing isolated MtrE proteins, with the method comprising culturing a host cell harboring a vector coding for the MtrE protein in culture conditions in which expression of the MtrE protein from the vector occurs in the host, and purifying the MtrE protein from the cell culture.

The present invention also directed to pharmaceutical composition comprising the isolated MtrE proteins of the present invention.

The present invention also provides therapeutic and prophylactic compositions, which may be antigenic compositions, and immunogenic compositions, including vaccines, for use in the treatment or prevention (reducing the likelihood) of *N. gonorrhoeae* infections in human subjects (patients). The immunogenic compositions include vaccines for use in humans. The antigenic and immunogenic, compositions of the present invention can be prepared by techniques known to those skilled in the art and comprise, for example, an immunologically effective amount of any of the MtrE immunogens disclosed herein, optionally in combination with or fused to or conjugated to one or more other immunogens, including lipids, phospholipids, carbohydrates, lipopolysaccharides, inactivated or attenuated whole organisms and other proteins, of *N. gonorrhoeae* origin or other bacterial origin, a pharmaceutically acceptable carrier, optionally an appropriate adjuvant, and optionally other materials traditionally found in vaccines.

In one embodiment, the invention provides a cocktail vaccine comprising several immunogens, which has the advantage that immunity against one or several strains of a single pathogen or one or several pathogens can be obtained by a single administration. Examples of other immunogens include, but are not limited to, those used in the known DPT vaccines, HMW protein of *C. trachomatis* or fragments thereof, MOMP of *C. trachomatis* or fragments thereof, or PMPH or HtrA of *C. trachomatis* or fragments thereof (preferably epitope containing fragments), entire organisms or subunits therefrom of *Chlamydia, Neisseria*, HIV, *Haemophilus influenzae, Moraxella catarrhalis*, Human papilloma virus, Herpes simplex virus, *Haemophilus ducreyi, Treponema palladium, Candida albicans* and *Streptococcus pneumoniae*, etc. The compositions may optionally comprise BIM protein or comprise an amino-terminal fragment of HMW protein, i.e., a fragment comprising or consisting of residues 1-100, 1-200, 1-300, 1-400, or 1-500 of the mature HMW protein.

In specific embodiments, the pharmaceutical or vaccine composition comprises an MtrE polypeptide and an HMW protein, or fragment thereof (for example at least 5, 8, 10, 20, 40, 50, 60, 80, 100, 150, 200, 300, 400 or 500 amino acid fragment with an epitope containing fragment thereof). In other specific embodiments, the composition comprises an MtrE polypeptide and a MOMP, or fragment thereof (for example an at least 5, 8, 10, 20, 40, 50, 60, 80, 100, 150, 200, 300, 400 or 500 amino acid fragment with an epitope containing fragment thereof).

The term "immunogenic amount" is used herein to mean an amount sufficient to induce an immune response to produce antibodies, T-cells, and/or cytokines and other cellular immune response components. In one embodiment, the immunogenic composition is one that elicits an immune response sufficient to prevent or reduce the likelihood of *N. gonorrhoeae* infections or to attenuate the severity of any preexisting or subsequent *N. gonorrhoeae* infection. An immunogenic amount of the immunogen to be used in the vaccine is determined by means known in the art in view of the teachings herein. The exact concentration will depend upon the specific immunogen to be administered, but can be determined by using standard techniques well known to those skilled in the art for assaying the development of an immune response.

The vaccine compositions of the invention elicit an immune response in a subject. Compositions which induce antibodies, including anti-MtrE protein antibodies and antibodies that are opsonizing or bactericidal are one aspect of the invention. In one non-limiting embodiment of the invention, an effective amount of a composition of the invention produces an elevation of antibody titer after administration. In another, more specific embodiment of the invention, approximately 0.01 to 2000 µg, or 0.1 to 500 µg, or 50 to 250 µg of the MtrE protein administered is to a host. Compositions which induce T-cell responses which are bactericidal or reactive with host cells infected with *N. gonorrhoeae* are also an aspect of the invention. Additional compositions comprise at least one adjuvant.

The combined immunogen and carrier or diluent may be an aqueous solution, emulsion or suspension or may be a dried preparation. Appropriate carriers are known to those skilled in the art and include stabilizers, diluents, and buffers. Suitable stabilizers include carbohydrates, such as sorbitol, lactose, mannitol, starch, sucrose, dextran, and glucose, and proteins, such as albumin or casein. Suitable diluents include saline, Hanks Balanced Salts, and Ringers solution. Suitable buffers include an alkali metal phosphate, an alkali metal carbonate, or an alkaline earth metal carbonate. In select embodiments, the composition of the invention is formulated for administration to humans.

The pharmaceutical and immunogenic compositions, including vaccines, of the invention are prepared by techniques known to those skilled in the art, given the teachings contained herein. Generally, an immunogen is mixed with the carrier to form a solution, suspension, or emulsion. One or more of the additives discussed herein may be added in the carrier or may be added subsequently. The vaccine preparations may be desiccated or lyophilized, for example, by freeze drying or spray drying for storage or formulations purposes. They may be subsequently reconstituted into liquid vaccines by the addition of an appropriate liquid carrier or administered in dry formulation using methods known to those skilled in the art, particularly in capsules or tablet forms.

An effective amount of the antigenic, immunogenic, pharmaceutical, including, but not limited to vaccine, composition of the invention should be administered, in which "effective amount" is defined as an amount that is sufficient to produce a desired prophylactic, therapeutic or ameliorative response in a subject, including but not limited to an immune response. The amount needed will vary depending upon the immunogenicity of the MtrE protein or nucleic acid used, and the species and weight of the subject to be administered, but may be ascertained using standard techniques.

Immunogenic, antigenic, pharmaceutical and vaccine compositions may further contain one or more auxiliary substance, such as wetting or emulsifying agents, pH buffering agents, or adjuvants to enhance the effectiveness thereof. Immunogenic, antigenic, pharmaceutical and vaccine compositions may be administered to birds, humans or other mammals, including ruminants, rodents or primates, by a variety of administration routes, including parenterally, intradermally, intraperitoneally, subcutaneously or intramuscularly.

Alternatively, the immunogenic, antigenic, pharmaceutical and vaccine compositions formed according to the present invention, may be formulated and delivered in a manner to evoke an immune response at mucosal surfaces. Thus, the immunogenic, antigenic, pharmaceutical and vaccine compositions may be administered to mucosal surfaces by, for example, the nasal, oral (intragastric), ocular, bronchiolar, intravaginal or intrarectal routes. Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose and magnesium carbonate. These compositions can take the form of microspheres, solutions, suspensions, tablets, pills, capsules, sustained release formulations or powders and contain about 0.001 to 95% of the MtrE protein. Some dosage forms may contain 50 µg to 250 µg of the MtrE protein. The immunogenic, antigenic, pharmaceutical and vaccine compositions are administered in a manner compatible with the dosage formulation, and in such amount as will be therapeutically effective, protective or immunogenic. The compositions may optionally comprise an adjuvant.

Further, the immunogenic, antigenic, pharmaceutical and vaccine compositions may be used in combination with or conjugated to one or more targeting molecules for delivery to specific cells of the immune system and/or mucosal surfaces. Some examples include but are not limited to vitamin B12, bacterial toxins or fragments thereof, monoclonal antibodies and other specific targeting lipids, proteins, nucleic acids or carbohydrates.

Suitable regimes for initial administration and booster doses are also variable, but may include an initial administration followed by subsequent administrations. The dose may also depend on the route(s) of administration and will vary according to the size of the host. The concentration of the MtrE protein in an antigenic, immunogenic or pharmaceutical composition according to the invention is in general about 0.001 to 95%, specifically about 0.01 to 5%.

The antigenic, immunogenic or pharmaceutical preparations, including vaccines, may comprise as the immunostimulating material a nucleic acid vector comprising at least a portion of the nucleic acid molecule encoding the MtrE protein.

A vaccine comprising nucleic acid molecules encoding one or more of the MtrE polypeptides of the present invention fusion proteins as described herein, such that the polypeptide is generated in situ is provided. In such vaccines, the nucleic acid molecules may be present within any of a variety of delivery systems known to those skilled in the art, including nucleic acid expression systems, bacterial and viral expression systems. Appropriate nucleic acid expression systems contain the necessary nucleotide sequences for expression in the patient such as suitable promoter and terminating signals. The nucleic acid molecules may be introduced using a viral expression system (e.g., vaccinia or other pox virus, alphavirus retrovirus or adenovirus) which may involve the use of non-pathogenic (defective) virus. Techniques for incorporating nucleic acid molecules into such expression systems are well known to those of ordinary skill in the art. The nucleic acid molecules may also be administered as "naked" plasmid vectors as described, for example, in Ulmer et al. Science 259:1745-1749 (1992) and reviewed by Cohen, Science 259:1691-1692 (1993). Techniques for incorporating DNA into such vectors are well known to those of ordinary skill in the art. A vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods know to those skilled in the art.

Nucleic acid molecules (DNA or RNA) of the invention can be administered as vaccines for therapeutic or prophylactic purpose. Typically a DNA molecule is placed under the control of a promoter suitable for expression in a mammalian cell. The promoter can function ubiquitously or tissue-specifically. Examples of non-tissue specific promoters include but are not limited to the early cytomegalovirus (CMV) promoter (described in U.S. Pat. No. 4,168,062) and Rous Sarcoma virus promoter (described in Norton and Coffin, Molec. Cell Biol. 5:281 (1985)). The desmin promoter (Li et al. Gene 78:243 (1989); Li & Paulin, J. Biol Chem 266:6562 (1991); and Li & Paulin, J. Biol Chem 268:10401 (1993)) is tissue specific and drives expression in muscle cells. More generally, useful vectors are described in, e.g., WO 94/21797 and Hartikka et al., Human Gene Therapy 7:1205 (1996).

A composition of the invention can contain one or several nucleic acid molecules of the invention. It can also contain at least one additional nucleic acid molecule encoding another antigen or fragment derivative, including but not limited to, DPT vaccines, HMW protein of *C. trachomatis* or fragment thereof, MOMP of *C. trachomatis* or fragment thereof, entire organisms or subunits therefrom of *Chlamydia, Neisseria*, HIV *Haemophilus influenzae, Moraxella catarrhalis*, Human papilloma virus, Herpes simplex virus, *Haemophilus ducreyi, Treponema pallidium, Candida albicans* and *Streptococcus pneumoniae*, etc. A nucleic acid molecule encoding a cytokine, such as interleukin-1 or interleukin-12 can also be added to the composition so that the immune response is enhanced. DNA molecules of the invention and/or additional DNA molecules may be on different plasmids or vectors in the same composition or can be carried in the same plasmid or vector.

Other formulations of nucleic acid molecules for therapeutic and prophylactic purposes include sterile saline or sterile buffered saline colloidal dispersion systems, such as macromolecule complexes, nanocapsules, silica microparticles, tungsten microparticles, gold microparticles, microspheres, beads and lipid based systems including oil-in-water emulsions, micelles, mixed micelles and liposomes. A preferred colloidal system for use as a delivery vehicle in vitro and in vivo is a liposome (i.e., an artificial vesicle). The uptake of naked nucleic acid molecules may be increased by incorporating the nucleic acid molecules into and/or onto biodegradable beads, which are efficiently transported into the cells. The preparation and use of such systems is well known in the art.

A nucleic acid molecule can be associated with agents that assist in cellular uptake. It can be formulated with a chemical agent that modifies the cellular permeability, such as bupivacaine (see, e.g., WO 94/16737).

Cationic lipids are also known in the art and are commonly used for DNA delivery. Such lipids include LIPOFECTIN™, also known as DOTMA (N-[1-(2,3-dioleyloxy) propyl]-N,N,N-trimethylammonium chloride), DOTAP (1,2-bis(oleyloxy)-3-(trimethylammonio)propane, DDAB (dimethyldioctadecylammonium bromide), DOGS (dioctadecylamidologlycy spermine) and cholesterol derivatives such as DC-Chol (3 beta-(N—(N',N'-dimethyl aminomethane)-carbamoyl) cholesterol. A description of these cationic lipids can be found in EP 187,702, WO 90/11092, U.S. Pat. No. 5,283,185, WO 91/15501, WO 95/26356, and U.S. Pat. No. 5,527,928. Cationic lipids for DNA delivery can be used in association with a neutral lipid such as DOPE (dioleyl phosphatidylethanolamine) as described in, e.g., WO 90/11092.

Other transfection facilitation compounds can be added to a formulation containing cationic liposomes. They include, e.g., spermine derivatives useful for facilitating the transport of DNA through the nuclear membrane (see, for example, WO 93/18759) and membrane-permeabilizing compounds such as GAL4, Gramicidine S and cationic bile salts (see, for example, WO 93/19768).

The amount of nucleic acid molecule to be used in a vaccine recipient depends, e.g., on the strength of the promoter used in the DNA construct, the immunogenicity of the expressed gene product, the mode of administration and type of formulation. In general, a therapeutically or prophylactically effective dose from about 1 µg to about 1 mg, preferably from about 10 µg to about 800 µg and more preferably from about 25 µg to about 250 µg can be administered to human adults. The administration can be achieved in a single dose or repeated at intervals.

The route of administration can be any conventional route used in the vaccine field. As general guidance, a nucleic acid molecule of the invention can be administered via a mucosal surface, e.g., an ocular, intranasal, pulmonary, oral, intestinal, rectal, vaginal, and urinary tract surface; or via a parenteral route, e.g., by an intravenous, subcutaneous, intraperitoneal, intradermal, intra-epidermal or intramuscular route. The choice of administration will depend on the formulation that is selected. For instance a nucleic acid molecule formulated in association with bupivacaine is advantageously administered into muscles.

Recombinant bacterial vaccines genetically engineered for recombinant expression of nucleic acid molecules encoding an MtrE protein of the present invention include *Shigella*, *Salmonella*, *Vibrio cholerae*, and *Lactobacillus*. Recombinant BCG and *Streptococcus* expressing MtrE polypeptides can also be used for prevention or treatment of *N. gonorrhoeae* infections.

Non-toxicogenic *Vibrio cholerae* mutant strains that are useful as a live oral vaccine are described in Mekalanos et al. Nature 306:551 (1983) and U.S. Pat. No. 4,882,278. An effective vaccine dose of a *Vibrio cholerae* strain capable of expressing a polypeptide or polypeptide derivative encoded by a DNA molecule of the invention can be administered.

Attenuated *Salmonella typhimurium* strains, genetically engineered for recombinant expression of heterologous antigens or not and their use as oral vaccines are described in Nakayama et al. Bio/Technology 6:693 (1988) and WO 92/11361.

Other bacterial strains useful as vaccine vectors are described in High et al., EMBO 11:1991 (1992); Sizemore et al., Science 270:299 (1995) (*Shigella flexneri*); Medaglini et al., Proc Natl. Acad. Sci. US 92:6868 (1995) (*Streptococcus gordonii*); and Flynn, Cell Mol. Biol. 40:31 (1994); WO 88/6626; WO 90/0594; WO 91/13157; WO 92/1796; and WO 02/21376 (Bacille Calmette Guerin).

In genetically engineered recombinant bacterial vectors, nucleic acid molecule(s) of the invention can be inserted into the bacterial genome, carried on a plasmid, or can remain in a free state.

When used as vaccine agents, recombinant bacterial or viral vaccines, nucleic acid molecules and polypeptides of the invention can be used sequentially or concomitantly as part of a multistep immunization process. For example, a mammal or bird can be initially primed with a vaccine vector of the invention such as pox virus or adenovirus, e.g., via the parenteral route or mucosally and then boosted several time with a polypeptide e.g., via the mucosal route. In another example, a mammal can be vaccinated with polypeptide via the mucosal route and at the same time or shortly thereafter, with a nucleic acid molecule via intramuscular route.

An adjuvant can also be added to a composition containing an MtrE vaccine. To efficiently induce humoral immune responses (HIR) and cell-mediated immunity (CMI), immunogens are typically emulsified in adjuvants. Immunogenicity can be significantly improved if the immunogen is co-administered with an adjuvant. Adjuvants may act by retaining the immunogen locally near the site of administration to produce a depot effect facilitating a slow, sustained release of antigen to cells of the immune system. Adjuvants can also attract cells of the immune system to an immunogen depot and stimulate such cells to elicit immune responses.

Many adjuvants are toxic, inducing granulomas, acute and chronic inflammations (Freund's complete adjuvant, FCA), cytolysis (saponins and Pluronic polymers) and pyrogenicity, arthritis and anterior uveitis (LPS and MDP).

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Aluminum hydroxide, aluminum oxide, and aluminum phosphate (collectively commonly referred to as alum) are routinely used as adjuvants in human and veterinary vaccines. The efficacy of alum in increasing antibody responses to diphtheria and tetanus toxoids is well established and a HBsAg vaccine has been adjuvanted with alum.

Other extrinsic adjuvants may include chemokines, cytokines (e.g., IL-2), saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes.

U.S. Pat. No. 6,019,982, incorporated herein by reference, describes mutated forms of heat labile toxin of enterotoxigenic *E. coli* ("mLT"). U.S. Pat. No. 5,057,540, incorporated herein by reference, describes the adjuvant, QS21, an HPLC purified non-toxic fraction of a saponin from the bark of the South American tree *Quiliaja saponaria* molina. 3D-MPL is described in Great Britain Patent 2,220,211, which is incorporated herein by reference.

U.S. Pat. No. 4,855,283 granted to Lockhoff et al. on Aug. 8, 1989, which is incorporated herein by reference, teaches glycolipid analogues including N-glycosylamides, N-glycosylureas and N-glycosylcarbamates, each of which is substituted in the sugar residue by an amino acid, as immunomodulators or adjuvants. Lockhoff reported that N-glycosphospholipids and glycoglycerolipids are capable of eliciting strong immune responses in both herpes simplex virus vaccine and pseudorabies virus vaccine. Some glycolipids have been synthesized from long chain-alkylamines and fatty acids that are linked directly with the sugars through the anomeric carbon atom, to mimic the functions of the naturally occurring lipid residues.

U.S. Pat. No. 4,258,029 granted to Moloney, incorporated herein by reference, teaches that octadecyl tyrosine hydrochloride (OTH) functions as an adjuvant when complexed with tetanus toxoid and formalin inactivated type I, II and III poliomyelitis virus vaccine. Lipidation of synthetic peptides has also been used to increase their immunogenicity.

Therefore, according to the invention, the immunogenic, antigenic, pharmaceutical, including vaccine, compositions comprising an MtrE protein, or an MtrE protein encoding nucleic acid or fragment thereof, vector or cell expressing the same, may further comprise an adjuvant, such as, but not limited to alum, mLT, LTR192G, QS21, R1131 DETOX™, MMPL, CpG DNA, MF59, calcium phosphate, PLG interleukin 12 (IL12), TLR7 imidazoquinoline ligand 3M-019, resquimod (R848), small molecule mast cell activator MP7 and all those listed above. The adjuvant may be selected from one or more of the following: alum, QS21, CpG DNA, PLG, LT, 3D-mPL, or Bacille Calmette-Guerine (BCG) and mutated or modified forms of the above, particularly mLT and LTR192G. The compositions of the present invention may also further comprise a suitable pharmaceutical carrier, including but not limited to saline, bicarbonate, dextrose or other aqueous solution. Other suitable pharmaceutical carriers are described in Remington's Pharmaceutical Sciences, Mack Publishing Company, a standard reference text in this field, which is incorporated herein by reference in its entirety.

Immunogenic, antigenic and pharmaceutical, including vaccine, compositions may be administered in a suitable, nontoxic pharmaceutical carrier, may be comprised in microcapsules, microbeads, and/or may be comprised in a sustained release implant.

Immunogenic, antigenic and pharmaceutical, including vaccine, compositions may desirably be administered at several intervals in order to sustain antibody levels and/or T-cell levels. Immunogenic, antigenic and pharmaceutical, including vaccine, compositions may be used in conjunction with other bacteriocidal or bacteriostatic methods.

Also included in the invention is a method of producing an immune response in an animal comprising immunizing the animal with an effective amount of one or more of the MtrE polypeptides or nucleic acid molecules encoding the MtrE polypeptides of the invention, compositions comprising the same and vaccines comprising the same. The MtrE polypeptides, nucleic acids, compositions and vaccines comprising the MtrE polypeptides of the invention may be administered simultaneously or sequentially. Examples of simultaneous administration include cases in which two or more polypeptides, nucleic acids, compositions, or vaccines, which may be the same or different, are administered in the same or different formulation or are administered separately, e.g., in a different or the same formulation but within a short time (such as minutes or hours) of each other. Examples of sequential administration include cases in which two or more polypeptides, nucleic acids, compositions or vaccines, which may be the same or different, are not administered together or within a short time of each other, but may be administered separately at intervals of, for example, days, weeks, months or years.

The polypeptides, nucleic acid molecules or recombinant bacterial vaccines of the present invention are also useful in the generation of antibodies, as described herein, or T-cells. For T-cells, animals, including humans, are immunized as described above. Following immunization, PBL (peripheral blood lymphocytes), spleen cells or lymph node cells are harvested and stimulated in vitro by placing large numbers of lymphocytes in flasks with media containing human serum. A polypeptide of the present invention is added to the flasks, and T-cells are harvested and placed in new flasks with X-irradiated peripheral blood mononuclear cells. The polypeptide is added directly to these flasks, and cells are grown in the presence of IL-2. As soon as the cells are shown to be *N. gonorrhoeae* specific T-cells, they are changed to a stimulation cycle with higher IL-2 concentrations (20 units) to expand them.

Alternatively, one or more T-cells that proliferate in the presence of a polypeptide of the present invention can be expanded in number by cloning. Methods for cloning cells are well known in the art. For example, T-cell lines may be established in vitro and cloned by limiting dilution. Responder T-cells are purified from the peripheral blood established in culture by stimulating with the nominal antigen in the presence of irradiated autologous filler cells. In order to generate CD4$^+$ T-cell lines, the MtrE polypeptides are used as the antigenic stimulus and autologous P3L or lymphoblastoid cell lines (LCL) immortalized by infection with Epstein Barr virus are used as antigen presenting cells. To generate CD8$^+$ T-cell lines, autologous antigen-presenting cells transfected with an expression vector which produces the relevant MtrE polypeptide may be used as stimulator cells. T-cell lines are established following antigen stimulation by plating stimulated T-cells in 96-well flat-bottom plates with PBL or LCL cells and recombinant interleukin-2 (rIL2) (50 U/ml). Wells with established clonal growth are identified at approximately 2-3 weeks after initial plating and restimulated with appropriate antigen in the presence of autologous antigen-presenting cells, then subsequently expanded by the addition of low doses of IL2. T-cell clones are maintained in 24-well plates by periodic restimulation with antigen and IL2 approximately every two weeks.

T-cell preparations may be further enriched by isolating T-cells specific for antigen reactivity using the methods disclosed by Kendricks et al. in U.S. Pat. No. 5,595,881.

The vaccine compositions of the present inventions are useful in preventing, treating or ameliorating disease symptoms in an animal, for example a human, with a disease or disorder associated with *N. gonorrhoeae* infection or to prevent the occurrence or progression of a disease or disorder associated with *N. gonorrhoeae* infection in an animal, for example a human.

The invention also provides for methods of inhibiting the growth of *N. gonorrhoeae*, with the methods comprising contacting the *N. gonorrhoeae* with the antibody-containing pharmaceutical compositions described herein.

The invention provides for methods of producing the isolated MtrE protein described herein, with the methods comprising culturing a host cell harboring a vector coding for the MtrE protein in culture conditions in which expression of the MtrE protein from the vector occurs in the host, and purifying the MtrE protein from the cell culture.

In one embodiment, the methods comprise culture conditions in which expression of the MtrE expression from the vector comprise culturing the host cell at a temperature below 37° C.

In another embodiment, the methods also comprise culture conditions in which expression of the MtrE expression from the vector comprise culturing the host cell for at least 8 hours.

In another embodiment, the methods also comprise culture conditions in which expression of the MtrE expression from the vector comprise culturing the host in a medium comprising an enzymatic digest of casein.

In another embodiment, the methods also comprise purifying the MtrE expression from the cell culture comprises lysing the host cells in the presence of at least two ionic detergents.

The invention also provides chimeric proteins comprising the MtrE peptides described herein. In one embodiment, the MtrE peptides described herein fused to a porin protein or fragment thereof. In particular, Porin B (PorB) sequences can be fused to the MtrE peptides described herein. *N. gonorrhoeae* strains are classified based on their PorB serotype, PorB1A and PorB1B, and within each serotype there are several antigenic variants due to differences in the amino acid sequences of surface-exposed regions. The PorB sequences that can be incorporated into or fused to the MtrE peptides include but are not limited to one or more surface-exposed loops of commonly expressed PorB1A or PorB1B molecules. Examples of the surface exposed loops that can be incorporated into or fused to the MtrE peptides of the present invention include but are not limited to those listed in Table VI below.

TABLE VI

Examples of PorB1A or PorB1B peptides genetically engineered into MtrE peptides

| Peptide | Sequence |
| --- | --- |
| PIA1 | TIKAGVETSRSVAHHGAQADRVKTA TEIADLG (SEQ ID NO: 5) |
| PIA2 | AIWQLEQKAYVSGTDTGWGNRQSFI GLKG (SEQ ID NO: 6) |
| PIA3 | VLKDTGGFNPWEGKSYYLGLSNIAQ PEERHVSV (SEQ ID NO: 7) |
| PIA5 | VQYAGFYKRHSYTTEKHQVHRLVGG YDH (SEQ ID NO: 8) |

TABLE VI-continued

Examples of PorB1A or PorB1B peptides genetically engineered into MtrE peptides

| Peptide | Sequence |
| --- | --- |
| PIA6 | SVAVQQQDAKLTWRNDNSHNSQTEV AATAA (SEQ ID NO: 9) |
| PIA7 | VSYAHGFKGSVYDADNDNTYDQVVV GAEYDF (SEQ ID NO: 10) |
| PIA8 | ALVSAGWLQRGKGTEKFVATVGGVG LRH (SEQ ID NO: 11) |
| PIA8-a | GKGTEK (SEQ ID NO: 12) |
| PIB2 | KAVWQLEQGASVAGTNTGWGNKQSF IGLKGGF (SEQ ID NO: 13) |
| PIB4 | AGFSGSVQYAPKDNSGSNGESYHVG LN (SEQ ID NO: 14) |
| PIB5 | GLFQRYGEGTKKIEYDGQTYSIPSL FVEKLQVHR (SEQ ID NO: 15) |
| PIB6 | AAQQQDAKLYGAMSGNSHNSQTEVA AT (SEQ ID NO: 16) |
| PIB7 | HGFKGTVDSANHDNTYDQVVVGAEY (SEQ ID NO: 17) |

In one specific embodiment, the chimeric proteins of the present invention comprise the sequence of MtrE with the PIA8-a sequence (loop 8 surface exposed residues on PorB1A) being fused into surface exposed Loop 1 of MtrE.

(SEQ ID NO: 4)
MNTTLKTTLT SVAAAFALSA CTMIPQYEQP KVEVAETFQN

DTSVSSIRAV DLGWHDYFAD PRLQKLIDIA LERNTSLRTA

VLNSEIYRKQ YMIERNNLLP TLAANANGSR QGSLSGGKGT

EKGNVSSSYN VGLGAASYEL DLFGRVRSSS EAALQGYFAS

VANRDAAHLS LIATVAKAYF NERYAEEAMS LAQRVLKTRE

ETYNAVRIAV QGRRDFRRRP APAEALIESA KADYAHAARS

REQARNALAT LINRPIPEDL PAGLPLDKQF FVEKLPAGLS

SEVLLDRPDI RAAEHALKQA NANIGAARAA FFPSIRLTGS

VGTGSVELGG LFKSGTGVWA FAPSITLPIF TWGTNKANLD

VAKLRQQAQI VAYESAVQSA FQDVANALAA REQLDKAYDA

LSKQSRASKE ALRLVGLRYK HGVSGALDLL DAERSSYSAE

GAALSAQLTR AENLADLYKA LGGGLKRDTQ TGK

In specific embodiments, the invention provides isolated protein fragments with amino acid sequences comprising or alternatively consisting of amino acid residues 23-473 of SEQ ID NO: 4, amino acid residues 23-161 of SEQ ID NO: 4 or an amino acid residues 319-473 of SEQ ID NO: 4. In other specific embodiments, the invention provides isolated MtrE peptides with amino acid sequences comprising or alternatively consisting of amino acid residues 112-124 of SEQ ID NO: 4.

In specific examples, the invention is directed to isolated variants of MtrE proteins comprising, or in the alternative consisting of an amino acid sequence that is at least 80% identical to residues 23-473 of SEQ ID NO: 4, or an amino acid sequence that is at least 80% identical to residues 23-161 of SEQ ID NO: 4. In additional embodiments, the invention is directed to isolated MtrE proteins that have amino acid sequences comprising, or in the alternative consisting of sequences, that are at least 85%, 86%, 87%, 88%, 89%, 90%, 91%, 92%, 93%, 94%, 95%, 96%, 97%, 98%, 99% and 100% identical to residues 23-473 of SEQ ID NO: 4. In more embodiments, the invention is directed to isolated MtrE proteins that have amino acid sequences comprising, or in the alternative consisting of sequences, that are at least 85%, 86%, 87%, 88%, 89%, 90%, 91%, 92%, 93%, 94%, 95%, 96%, 97%, 98%, 99% and 100% identical to residues 23-161 of SEQ ID NO: 4. In still more embodiments, the invention is directed to isolated MtrE proteins that have amino acid sequences comprising, or in the alternative consisting of sequences, that are at least 85%, 86%, 87%, 88%, 89%, 90%, 91%, 92%, 93%, 94%, 95%, 96%, 97%, 98%, 99% and 100% identical to residues 112-124 of SEQ ID NO: 4.

EXAMPLES

Example 1—Construction of MtrE Expression Plasmids

The mtrE expression plasmid, pETAD-1, was constructed by PCR amplification of a previously described mtrE plasmid, pCR-mtrE (Warner et al., 2007). The forward primer, oAJD-36 (GGCAATGTCATGATCCTCAATAC-GAGCAGC (SEQ ID NO: 18)) contains a BspHI site (indicated in boldface type) and amplifies mtrE from residue 3 (methionine) of the mature protein. The reverse primer, oAJD-18 (ATAGTTTAGCGGCCGCTTTGCCG-GTTTGGGTATCCC (SEQ ID NO: 19)) contains a NotI site (indicated in boldface type), and amplifies mtrE from the final residue (residue 447-lysine). PCR was performed with Taq polymerase (Qiagen) and the resulting PCR product was ligated into pET28 b+(EMD Biosciences) to create expression plasmid pETAD-1. pETAD-1 encodes a recombinant MtrE protein under the control of a T7 promoter that lacks the amino terminal signal sequence and has 5 additional residues encoded by pET28 b+ immediately prior to the C-terminal six-histidine tag to provide restriction site compatibility (C-terminal sequence: AAALEHHHHHH (SEQ ID NO: 20)).

The pETAD-2 (truncated N-terminal recombinant MtrE) and pETAD-3 (truncated C-terminal recombinant MtrE) expression vectors were constructed in the manner described above. To create pETAD-2, PCR amplification was performed with the forward primer oAJD-36 (described above) and the reverse primer oAJD-37 (ATAGTTTAGCGGCCG-CAACGCTGGCAAAATAGCC (SEQ ID NO: 21)) which contains a NotI site (indicated in boldface type). The resulting construct encodes a recombinant, truncated MtrE (residues 3-135) fused to the C-terminal sequence AAALEHH-HHHH, incorporating a six-histidine tag. pETAD-3 was created by PCR amplification with the forward primer oAJD-38 (CATGCCATGGGCAGCGTCGGTACGGG (SEQ ID NO: 22)) which contains a NcoI site (indicated in boldface type) and reverse primer oAJD-18 (described above). The resulting construct encodes a recombinant, truncated MtrE (residues 293-447) fused to the C-terminal sequence AAALEHHHHHH (SEQ ID NO: 20), incorporating a six-histidine tag.

All other vectors encoding various lengths of recombinant MtrE are constructed in a manner similar to that described above, utilizing PCR amplification and commercially-available vectors. The expression hosts for the pETAD vectors were commercially available *E. coli* strains including, but not limited to BL21 (DE3) (EMD Millipore).

Example 2—Construction of MtrE-PorB Expression Plasmids

MtrE-PorB fusion proteins will be created using a Gene SOEing (Horton et al., 1990) technique where the porin loop sequence is encoded by the primers. The mtrE coding sequence will be amplified from the pCR-mtrE plasmid (Warner et al., 2007) using a two-step PCR method with the outside primers oAJD-36 and oAJD-18. The PorB loop sequence will be incorporated at either of putative loop regions of MtrE in a manner that does not compromise the integrity of this surface-exposed domain. In select constructs, the PorB loop sequences are added to the N-terminus of recombinant MtrE proteins. In select constructs, the PorB loop sequences are added to the C-terminus of recombinant MtrE proteins. In additional select constructs, the PorB loop sequences are added internal to the recombinant MtrE proteins.

Examples of PorB loop sequences that will be incorporated into the MtrE proteins are shown in Table VI above.

Example 3—Recombinant Protein Expression and Purification

Recombinant MtrE proteins were expressed using baffled flasks containing 400 ml of NZCYM broth (pH 7.0) with 30 µg/ml kanamycin. Once cultures reached a 600 nm optical density of 0.6 to 0.9, IPTG (isopropyl-β-d-thiogalactopyranoside) was added to 0.5 mM. Expression proceeded overnight (~18 hrs) at 25° C. Following expression, bacteria were pelleted by centrifugation at 10,000×g for 10 minutes at 4° C. Cell pellets were then stored overnight at −80° C.

MtrE was purified by thawing the pellets on ice and suspension of the bacterial cell pellet in BugBuster (EMD Millipore), 5 ml/gram pellet weight. Lysozyme (Sigma) 0.5 mg/ml, benzonase (EMD Millipore) 1 µl/ml, and protease inhibitors (EMD Millipore) were added and the suspension was incubated at room temperature for 20-30 minutes on a rocking platform. Insoluble debris/proteins were removed by centrifugation at 16,000×g for 20 minutes at 4° C. The supernatant was removed for purification of soluble MtrE while the pellet was stored at −80° C. for purification of insoluble MtrE.

Soluble MtrE was purified by adding the supernatant to a Ni-NTA resin (EMD Millipore), equilibrated with binding buffer (300 mM NaCl, 50 mM $NaH_2PO_4$, 10 mM imidizole; pH 8.0), incubated 60 minutes, rocking at 4° C. The bound protein was washed twice with 20 bed volumes of wash buffer (300 mM NaCl, 50 mM $NaH_2PO_4$, 20 mM imidizole; pH 8.0) and eluted (300 mM NaCl, 50 mM $NaH_2PO_4$, 200 mM imidizole; pH 8.0). All buffers contained 0.7% n-Dodecyl-β-D-Maltopyranoside (Affymetrix). Following purification the protein was run through a buffer exchange desalting column (Pierce) and stored in PBS+0.7% n-Dodecyl-β-D-Maltopyranoside at −20° C. Protein concentration was determined by Nanodrop using the extinction coefficient of the protein.

MtrE was purified from inclusion bodies (insoluble MtrE) by thawing the insoluble debris/protein pellet described above on ice. The pellet was suspended in BugBuster (EMD Millipore), 5 ml/gram of pellet. Lysozyme (0.5 mg/ml) and protease inhibitors (EMD Millipore) were added and the suspension was incubated at room temperature for 5 minutes. Following incubation 6 volumes of 1:10 diluted Bug- Buster were added and the solution was subjected to centrifugation at 16,000×g for 15 minutes, 4° C. The supernatant was removed, and the resuspension and centrifugation were repeated two additional times. The resulting inclusion bodies were suspended in 6M Gu-HCL to denature the protein. MtrE was re-natured using a single-step dialysis method. The denatured protein was diluted 1:2 in 6M Gu-HCL, added to a Slide-A-Lyzer (20 k molecular weight cut off) dialysis cassette (Pierce) and dialyzed against 100-fold excess binding buffer+0.7% n-Dodecyl-β-D-Maltopyranoside at 4° C. overnight. The buffer was exchanged once and precipitate was removed by centrifugation at 12,000×g for 10 minutes, 4° C. Following overnight dialysis precipitate was once again removed by centrifugation and the protein was bound to Ni-NTA resin (EMD Millipore) using the protocol and buffers described above for purification of soluble MtrE.

Example 4—Immunization

Female BALB/c mice (National Cancer Institute, Bethesda, Md.) were immunized either subcutaneously (SQ) (systemic immunization) or intranasally (IN) (mucosal immunization) with MtrE purified from either the soluble or insoluble fractions at a dose of 10-30 μg/mouse. The following adjuvants were used: TiterMax Gold (CytRx) (SQ only), a water-in-oil adjuvant (dose: ≥50% of total immunization volume); Monophosphoryl A (MplA), a TLR4 agonist approved for human use (dose: 25 μg/mouse); Cholera Toxin (CT), a potent mucosal adjuvant (dose: 1 μg/mouse). Of course, other adjuvants can also be used, including but not limited to, IL-12, CpG (ODN 1826), imidazoquinoline compound 3M-019, MP7, resiquimod (R848).

Example 5—Production of Antisera Against Predicted Surface-exposed MtrE Loops

The surface-exposed MtrE loop sequences were predicted as follows. The outer membrane proteins ToIC (*E. coli*) and OprM (*Pseudomonas aeruginosa*), which are functionally similar to MtrE, are predicted to form two surface-exposed loops. The MtrE predicted amino acid sequence is most closely related to *P. aeruginosa*, thus regions in the predicted amino acid sequence of MtrE with homology to the four transmembrane regions that flank the two surface exposed loops in OprM were sought. Four regions were found in MtrE with homology to the OprM™ sequences S1, S2, S3 and S4, and the intervening sequences in the MtrE protein [GSLSGGN (SEQ ID NO: 2) (predicted surface loop 1, amino acids 112-118) and GSVGTGSVELGGLFKSGTGV (SEQ ID NO: 3) (predicted surface loop 2; amino acids 313-332)] were identified as potentially being surface-exposed. These predictions were supported by in silico analysis of the predicted structure. Affinity-purified rabbit antibodies against linear peptides that correspond to these regions were produced commercially (Bethyl laboratories) and tested by Western blot to confirm the specificity of the antisera.

Example 6—Bactericidal Assay

Bactericidal assays were performed as described previously (Cole and Jerse, 2009) with serum obtained by retroorbital bleed from mice immunized with MtrE. Normal human serum (NHS) was used as the complement source at the following concentrations: gonococcal strain FA1090, 4%; strain FA19, 10%; strain MS11, 1%; strain RD-1 (MtrE⁻), 10%. Heat Inactivated NHS was used as a control. Assays were performed in triplicate and the dilution of anti-MtrE serum resulting in 50% killing of the bacteria was reported.

Example 7—Surface Binding

To examine whether MtrE-specific mouse antibodies recognize the gonococcal surface, a flow cytometry assay was used. Briefly, wild type and MtrE-deficient *N. gonorrhoeae* strains were grown to mid-log phase and filtered through a 1.2 μm filter. Bacteria were added to a 96-well plate and subjected to centrifugation at 1500 RPM. The bacteria were suspended in serum (1:50-1:100 dilution) for 1 hour at room temperature. Bacteria were washed in 1% BSA (Ig-free, Sigma) and suspended in Alexa 488-conjugated anti-mouse secondary (1:250, Molecular Probes) for 30 minutes. Bacteria were then washed as described above and re-suspended in 100 μl HBSS2+ before addition of 4% paraformaldehyde. Normal mouse serum was used as a control for surface binding. Samples were analyzed using a BD LSRII cytometer.

Example 8—Inhibition of Efflux Pump Function

To test whether MtrE-specific antisera could increase the susceptibility of *N. gonorrhoeae* to the bactericidal activity of human cathelicidin LL37 (hLL37) by blocking MtrCDE efflux pump function, bacteria were suspended in minimal essential medium (MEM) and added to eppendorf tubes that contained MEM alone or MEM containing decreasing concentrations of antisera against the loop 1- or loop 2-peptides ($2.5 \times 10^5$ CFU per tube). Antiserum to a peptide that corresponds to the semivariable (SV) loop of the gonococcal Opa proteins (Opa$_{SV}$) (Cole and Jerse, 2009) was used as a negative control. Following 20 min incubation at 37° C., the bacterial suspensions were pipetted into a microtiter plate containing increasing concentrations of hLL37 (0 to 12.5 ug/ml); final concentration of bacteria per well: $3 \times 10^4$ CFU. The microtiter plates were incubated for 1 hr at 37° C. after which a constant volume of GCB was added and 25 μl of the final suspensions were inoculated onto GC agar. The number of CFU recovered from each concentration of hLL37 following overnight incubation was determined.

Example 9—Construction of MtrE-Porin Expression Plasmids

A MtrE-Porin fusion protein where Loop 8A from PorB was fused to Loop1 of MtrE was created as described in the construction of MtrE-PorB expression plasmids methods. The porin P1A8a sequence was incorporated at residue 96, fusing the porin epitope to the first putative surface-exposed domain of MtrE. Recombinant protein was expressed and purified as described in Example 3 above.

What is claimed is:

1. A vector comprising a polynucleotide encoding an MtrE protein or a fragment of an MtrE protein, wherein the fragment comprises the amino acid sequence of residues 313-467 of SEQ ID NO: 1.

2. The vector of claim 1, wherein the MtrE protein is SEQ ID NO: 1.

3. The vector of claim 1 wherein the polynucleotide encodes a fragment of an MtrE protein consisting of the amino acid sequence of residues 23-467 of SEQ ID NO: 1.

4. The vector of claim 1 wherein the polynucleotide encodes the amino acid sequence of residues 313-467 of SEQ ID NO: 1.

5. A host cell comprising the vector of claim 1.

6. The host cell of claim 5 wherein the host cell is an *E. coli* cell.

7. A vector comprising a polynucleotide encoding an amino acid sequence that is at least 95% identical to residues 23-467 of SEQ ID NO:1.

8. The vector of claim 7, wherein the amino acid sequence is at least 99% identical to residues 23-467 of SEQ ID NO:1.

9. A host cell comprising the vector of claim 7.

10. The host cell of claim 7 wherein the host cell is an *E. coli* cell.

* * * * *

SEQUENCE LISTING

<160> NUMBER OF SEQ ID NOS: 23

<210> SEQ ID NO 1
<211> LENGTH: 467
<212> TYPE: PRT
<213> ORGANISM: Neisseria gonorrhoeae

<400> SEQUENCE: 1

```
Met Asn Thr Thr Leu Lys Thr Thr Leu Thr Ser Val Ala Ala Ala Phe
1               5                   10                  15

Ala Leu Ser Ala Cys Thr Met Ile Pro Gln Tyr Glu Gln Pro Lys Val
            20                  25                  30

Glu Val Ala Glu Thr Phe Gln Asn Asp Thr Ser Val Ser Ser Ile Arg
        35                  40                  45

Ala Val Asp Leu Gly Trp His Asp Tyr Phe Ala Asp Pro Arg Leu Gln
    50                  55                  60

Lys Leu Ile Asp Ile Ala Leu Glu Arg Asn Thr Ser Leu Arg Thr Ala
65                  70                  75                  80

Val Leu Asn Ser Glu Ile Tyr Arg Lys Gln Tyr Met Ile Glu Arg Asn
                85                  90                  95

Asn Leu Leu Pro Thr Leu Ala Ala Asn Ala Asn Gly Ser Arg Gln Gly
            100                 105                 110

Ser Leu Ser Gly Gly Asn Val Ser Ser Tyr Asn Val Gly Leu Gly
            115                 120                 125

Ala Ala Ser Tyr Glu Leu Asp Leu Phe Gly Arg Val Arg Ser Ser Ser
        130                 135                 140

Glu Ala Ala Leu Gln Gly Tyr Phe Ala Ser Val Ala Asn Arg Asp Ala
145                 150                 155                 160

Ala His Leu Ser Leu Ile Ala Thr Val Ala Lys Ala Tyr Phe Asn Glu
                165                 170                 175

Arg Tyr Ala Glu Glu Ala Met Ser Leu Ala Gln Arg Val Leu Lys Thr
            180                 185                 190

Arg Glu Glu Thr Tyr Asn Ala Val Arg Ile Ala Val Gln Gly Arg Arg
        195                 200                 205

Asp Phe Arg Arg Pro Ala Pro Ala Glu Ala Leu Ile Glu Ser Ala
    210                 215                 220

Lys Ala Asp Tyr Ala His Ala Ala Arg Ser Glu Gln Ala Arg Asn
225                 230                 235                 240

Ala Leu Ala Thr Leu Ile Asn Arg Pro Ile Pro Glu Asp Leu Pro Ala
                245                 250                 255

Gly Leu Pro Leu Asp Lys Gln Phe Phe Val Glu Lys Leu Pro Ala Gly
            260                 265                 270

Leu Ser Ser Glu Val Leu Leu Asp Arg Pro Asp Ile Arg Ala Ala Glu
        275                 280                 285

His Ala Leu Lys Gln Ala Asn Ala Asn Ile Gly Ala Ala Arg Ala Ala
    290                 295                 300

Phe Phe Pro Ser Ile Arg Leu Thr Gly Ser Val Gly Thr Gly Ser Val
305                 310                 315                 320

Glu Leu Gly Gly Leu Phe Lys Ser Gly Thr Gly Val Trp Ala Phe Ala
                325                 330                 335

Pro Ser Ile Thr Leu Pro Ile Phe Thr Trp Gly Thr Asn Lys Ala Asn
            340                 345                 350

Leu Asp Val Ala Lys Leu Arg Gln Gln Ala Gln Ile Val Ala Tyr Glu
        355                 360                 365
```

```
Ser Ala Val Gln Ser Ala Phe Gln Asp Val Ala Asn Ala Leu Ala Ala
        370                 375                 380

Arg Glu Gln Leu Asp Lys Ala Tyr Asp Ala Leu Ser Lys Gln Ser Arg
385                 390                 395                 400

Ala Ser Lys Glu Ala Leu Arg Leu Val Gly Leu Arg Tyr Lys His Gly
                405                 410                 415

Val Ser Gly Ala Leu Asp Leu Leu Asp Ala Glu Arg Ser Ser Tyr Ser
                420                 425                 430

Ala Glu Gly Ala Ala Leu Ser Ala Gln Leu Thr Arg Ala Glu Asn Leu
                435                 440                 445

Ala Asp Leu Tyr Lys Ala Leu Gly Gly Leu Lys Arg Asp Thr Gln
450                 455                 460

Thr Gly Lys
465

<210> SEQ ID NO 2
<211> LENGTH: 7
<212> TYPE: PRT
<213> ORGANISM: Neisseria gonorrhoeae

<400> SEQUENCE: 2

Gly Ser Leu Ser Gly Gly Asn
1               5

<210> SEQ ID NO 3
<211> LENGTH: 20
<212> TYPE: PRT
<213> ORGANISM: Neisseria gonorrhoeae

<400> SEQUENCE: 3

Gly Ser Val Gly Thr Gly Ser Val Glu Leu Gly Gly Leu Phe Lys Ser
1               5                   10                  15

Gly Thr Gly Val
            20

<210> SEQ ID NO 4
<211> LENGTH: 473
<212> TYPE: PRT
<213> ORGANISM: Artificial Sequence
<220> FEATURE:
<223> OTHER INFORMATION: Synthetic sequence (Fusion protein - MtrE and
      PIA8-a)

<400> SEQUENCE: 4

Met Asn Thr Thr Leu Lys Thr Thr Leu Thr Ser Val Ala Ala Ala Phe
1               5                   10                  15

Ala Leu Ser Ala Cys Thr Met Ile Pro Gln Tyr Glu Gln Pro Lys Val
                20                  25                  30

Glu Val Ala Glu Thr Phe Gln Asn Asp Thr Ser Val Ser Ser Ile Arg
            35                  40                  45

Ala Val Asp Leu Gly Trp His Asp Tyr Phe Ala Asp Pro Arg Leu Gln
        50                  55                  60

Lys Leu Ile Asp Ile Ala Leu Glu Arg Asn Thr Ser Leu Arg Thr Ala
65                  70                  75                  80

Val Leu Asn Ser Glu Ile Tyr Arg Lys Gln Tyr Met Ile Glu Arg Asn
                85                  90                  95

Asn Leu Leu Pro Thr Leu Ala Ala Asn Ala Asn Gly Ser Arg Gln Gly
            100                 105                 110

Ser Leu Ser Gly Gly Lys Gly Thr Glu Lys Gly Asn Val Ser Ser Ser
```

```
            115                 120                 125
Tyr Asn Val Gly Leu Gly Ala Ala Ser Tyr Glu Leu Asp Leu Phe Gly
        130                 135                 140
Arg Val Arg Ser Ser Glu Ala Ala Leu Gln Gly Tyr Phe Ala Ser
145                 150                 155                 160
Val Ala Asn Arg Asp Ala Ala His Leu Ser Leu Ile Ala Thr Val Ala
                165                 170                 175
Lys Ala Tyr Phe Asn Glu Arg Tyr Ala Glu Ala Met Ser Leu Ala
            180                 185                 190
Gln Arg Val Leu Lys Thr Arg Glu Glu Thr Tyr Asn Ala Val Arg Ile
                195                 200                 205
Ala Val Gln Gly Arg Arg Asp Phe Arg Arg Pro Ala Pro Ala Glu
        210                 215                 220
Ala Leu Ile Glu Ser Ala Lys Ala Asp Tyr Ala His Ala Ala Arg Ser
225                 230                 235                 240
Arg Glu Gln Ala Arg Asn Ala Leu Ala Thr Leu Ile Asn Arg Pro Ile
                245                 250                 255
Pro Glu Asp Leu Pro Ala Gly Leu Pro Leu Asp Lys Gln Phe Phe Val
            260                 265                 270
Glu Lys Leu Pro Ala Gly Leu Ser Ser Glu Val Leu Leu Asp Arg Pro
        275                 280                 285
Asp Ile Arg Ala Ala Glu His Ala Leu Lys Gln Ala Asn Ala Asn Ile
        290                 295                 300
Gly Ala Ala Arg Ala Ala Phe Phe Pro Ser Ile Arg Leu Thr Gly Ser
305                 310                 315                 320
Val Gly Thr Gly Ser Val Glu Leu Gly Gly Leu Phe Lys Ser Gly Thr
                325                 330                 335
Gly Val Trp Ala Phe Ala Pro Ser Ile Thr Leu Pro Ile Phe Thr Trp
            340                 345                 350
Gly Thr Asn Lys Ala Asn Leu Asp Val Ala Lys Leu Arg Gln Gln Ala
                355                 360                 365
Gln Ile Val Ala Tyr Glu Ser Ala Val Gln Ser Ala Phe Gln Asp Val
        370                 375                 380
Ala Asn Ala Leu Ala Ala Arg Glu Gln Leu Asp Lys Ala Tyr Asp Ala
385                 390                 395                 400
Leu Ser Lys Gln Ser Arg Ala Ser Lys Glu Ala Leu Arg Leu Val Gly
                405                 410                 415
Leu Arg Tyr Lys His Gly Val Ser Gly Ala Leu Asp Leu Leu Asp Ala
            420                 425                 430
Glu Arg Ser Ser Tyr Ser Ala Glu Gly Ala Ala Leu Ser Ala Gln Leu
        435                 440                 445
Thr Arg Ala Glu Asn Leu Ala Asp Leu Tyr Lys Ala Leu Gly Gly Gly
        450                 455                 460
Leu Lys Arg Asp Thr Gln Thr Gly Lys
465                 470

<210> SEQ ID NO 5
<211> LENGTH: 32
<212> TYPE: PRT
<213> ORGANISM: Artificial Sequence
<220> FEATURE:
<223> OTHER INFORMATION: Synthetic sequence

<400> SEQUENCE: 5

Thr Ile Lys Ala Gly Val Glu Thr Ser Arg Ser Val Ala His His Gly
```

```
1               5                   10                  15
Ala Gln Ala Asp Arg Val Lys Thr Ala Thr Glu Ile Ala Asp Leu Gly
            20                  25                  30

<210> SEQ ID NO 6
<211> LENGTH: 29
<212> TYPE: PRT
<213> ORGANISM: Artificial Sequence
<220> FEATURE:
<223> OTHER INFORMATION: Synthetic sequence

<400> SEQUENCE: 6

Ala Ile Trp Gln Leu Glu Gln Lys Ala Tyr Val Ser Gly Thr Asp Thr
1               5                   10                  15

Gly Trp Gly Asn Arg Gln Ser Phe Ile Gly Leu Lys Gly
            20                  25

<210> SEQ ID NO 7
<211> LENGTH: 33
<212> TYPE: PRT
<213> ORGANISM: Artificial Sequence
<220> FEATURE:
<223> OTHER INFORMATION: Synthetic sequence

<400> SEQUENCE: 7

Val Leu Lys Asp Thr Gly Gly Phe Asn Pro Trp Glu Gly Lys Ser Tyr
1               5                   10                  15

Tyr Leu Gly Leu Ser Asn Ile Ala Gln Pro Glu Glu Arg His Val Ser
            20                  25                  30

Val

<210> SEQ ID NO 8
<211> LENGTH: 28
<212> TYPE: PRT
<213> ORGANISM: Artificial Sequence
<220> FEATURE:
<223> OTHER INFORMATION: Synthetic sequence

<400> SEQUENCE: 8

Val Gln Tyr Ala Gly Phe Tyr Lys Arg His Ser Tyr Thr Thr Glu Lys
1               5                   10                  15

His Gln Val His Arg Leu Val Gly Gly Tyr Asp His
            20                  25

<210> SEQ ID NO 9
<211> LENGTH: 30
<212> TYPE: PRT
<213> ORGANISM: Artificial Sequence
<220> FEATURE:
<223> OTHER INFORMATION: Synthetic sequence

<400> SEQUENCE: 9

Ser Val Ala Val Gln Gln Gln Asp Ala Lys Leu Thr Trp Arg Asn Asp
1               5                   10                  15

Asn Ser His Asn Ser Gln Thr Glu Val Ala Ala Thr Ala Ala
            20                  25                  30

<210> SEQ ID NO 10
<211> LENGTH: 31
<212> TYPE: PRT
<213> ORGANISM: Artificial Sequence
<220> FEATURE:
<223> OTHER INFORMATION: Synthetic sequence
```

```
<400> SEQUENCE: 10

Val Ser Tyr Ala His Gly Phe Lys Ser Val Tyr Asp Ala Asp Asn
1               5                   10                  15

Asp Asn Thr Tyr Asp Gln Val Val Gly Ala Glu Tyr Asp Phe
            20                  25                  30

<210> SEQ ID NO 11
<211> LENGTH: 28
<212> TYPE: PRT
<213> ORGANISM: Artificial Sequence
<220> FEATURE:
<223> OTHER INFORMATION: Synthetic sequence

<400> SEQUENCE: 11

Ala Leu Val Ser Ala Gly Trp Leu Gln Arg Gly Lys Gly Thr Glu Lys
1               5                   10                  15

Phe Val Ala Thr Val Gly Gly Val Gly Leu Arg His
            20                  25

<210> SEQ ID NO 12
<211> LENGTH: 6
<212> TYPE: PRT
<213> ORGANISM: Artificial Sequence
<220> FEATURE:
<223> OTHER INFORMATION: Synthetic sequence

<400> SEQUENCE: 12

Gly Lys Gly Thr Glu Lys
1               5

<210> SEQ ID NO 13
<211> LENGTH: 32
<212> TYPE: PRT
<213> ORGANISM: Artificial Sequence
<220> FEATURE:
<223> OTHER INFORMATION: Synthetic sequence

<400> SEQUENCE: 13

Lys Ala Val Trp Gln Leu Glu Gln Gly Ala Ser Val Ala Gly Thr Asn
1               5                   10                  15

Thr Gly Trp Gly Asn Lys Gln Ser Phe Ile Gly Leu Lys Gly Gly Phe
            20                  25                  30

<210> SEQ ID NO 14
<211> LENGTH: 27
<212> TYPE: PRT
<213> ORGANISM: Artificial Sequence
<220> FEATURE:
<223> OTHER INFORMATION: Synthetic sequence

<400> SEQUENCE: 14

Ala Gly Phe Ser Gly Ser Val Gln Tyr Ala Pro Lys Asp Asn Ser Gly
1               5                   10                  15

Ser Asn Gly Glu Ser Tyr His Val Gly Leu Asn
            20                  25

<210> SEQ ID NO 15
<211> LENGTH: 34
<212> TYPE: PRT
<213> ORGANISM: Artificial Sequence
<220> FEATURE:
<223> OTHER INFORMATION: Synthetic sequence

<400> SEQUENCE: 15
```

Gly Leu Phe Gln Arg Tyr Gly Glu Gly Thr Lys Lys Ile Glu Tyr Asp
1               5                   10                  15

Gly Gln Thr Tyr Ser Ile Pro Ser Leu Phe Val Glu Lys Leu Gln Val
            20                  25                  30

His Arg

<210> SEQ ID NO 16
<211> LENGTH: 27
<212> TYPE: PRT
<213> ORGANISM: Artificial Sequence
<220> FEATURE:
<223> OTHER INFORMATION: Synthetic sequence

<400> SEQUENCE: 16

Ala Ala Gln Gln Gln Asp Ala Lys Leu Tyr Gly Ala Met Ser Gly Asn
1               5                   10                  15

Ser His Asn Ser Gln Thr Glu Val Ala Ala Thr
            20                  25

<210> SEQ ID NO 17
<211> LENGTH: 25
<212> TYPE: PRT
<213> ORGANISM: Artificial Sequence
<220> FEATURE:
<223> OTHER INFORMATION: Synthetic sequence

<400> SEQUENCE: 17

His Gly Phe Lys Gly Thr Val Asp Ser Ala Asn His Asp Asn Thr Tyr
1               5                   10                  15

Asp Gln Val Val Val Gly Ala Glu Tyr
            20                  25

<210> SEQ ID NO 18
<211> LENGTH: 30
<212> TYPE: DNA
<213> ORGANISM: Artificial Sequence
<220> FEATURE:
<223> OTHER INFORMATION: Synthetic sequence (forward primer)

<400> SEQUENCE: 18
ggcaatgtca tgatcctcaa tacgagcagc                                    30

<210> SEQ ID NO 19
<211> LENGTH: 36
<212> TYPE: DNA
<213> ORGANISM: Artificial Sequence
<220> FEATURE:
<223> OTHER INFORMATION: Synthetic sequence (reverse primer)

<400> SEQUENCE: 19
atagtttagc ggccgctttg ccggtttggg tatccc                             36

<210> SEQ ID NO 20
<211> LENGTH: 11
<212> TYPE: PRT
<213> ORGANISM: Artificial Sequence
<220> FEATURE:
<223> OTHER INFORMATION: Synthetic sequence (C-terminal sequence)

<400> SEQUENCE: 20

Ala Ala Ala Leu Glu His His His His His His
1               5                   10

<210> SEQ ID NO 21

```
<211> LENGTH: 34
<212> TYPE: DNA
<213> ORGANISM: Artificial Sequence
<220> FEATURE:
<223> OTHER INFORMATION: Synthetic sequence (reverse primer)

<400> SEQUENCE: 21
atagtttagc ggccgcaacg ctggcaaaat agcc                               34

<210> SEQ ID NO 22
<211> LENGTH: 26
<212> TYPE: DNA
<213> ORGANISM: Artificial Sequence
<220> FEATURE:
<223> OTHER INFORMATION: Synthetic sequence (forward primer)

<400> SEQUENCE: 22
catgccatgg gcagcgtcgg tacggg                                        26

<210> SEQ ID NO 23
<211> LENGTH: 29
<212> TYPE: PRT
<213> ORGANISM: Artificial Sequence
<220> FEATURE:
<223> OTHER INFORMATION: Fusion Polypeptide

<400> SEQUENCE: 23

Leu Ala Ala Asn Ala Asn Gly Ser Arg Gln Gly Ser Leu Ser Gly Gly
1               5                   10                  15

Lys Gly Thr Glu Lys Gly Asn Val Ser Ser Ser Tyr Asn
            20                  25
```